(12) United States Patent
Aoki

(10) Patent No.: US 10,674,044 B2
(45) Date of Patent: Jun. 2, 2020

(54) OBSERVATION APPARATUS, METHOD FOR CONTROLLING OBSERVATION APPARATUS, AND NON-TRANSITORY COMPUTER-READABLE MEDIUM STORING CONTROL PROGRAM FOR OBSERVATION APPARATUS

(71) Applicant: OLYMPUS CORPORATION, Hachioji-shi, Tokyo (JP)

(72) Inventor: Takato Aoki, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 316 days.

(21) Appl. No.: 15/637,095

(22) Filed: Jun. 29, 2017

(65) Prior Publication Data

US 2018/0013930 A1   Jan. 11, 2018

(30) Foreign Application Priority Data

Jul. 11, 2016   (JP) .................................. 2016-137117

(51) Int. Cl.
*G06K 9/00* (2006.01)
*H04N 3/14* (2006.01)
(Continued)

(52) U.S. Cl.
CPC ....... *H04N 3/1587* (2013.01); *G02B 21/0032* (2013.01); *G06K 9/00127* (2013.01);
(Continued)

(58) Field of Classification Search
CPC .... G06K 9/00127; G06K 9/20; G06K 9/2009; G06K 9/209; G06K 7/01; G06K 7/015;
(Continued)

(56) References Cited

U.S. PATENT DOCUMENTS

| 5,397,709 A * | 3/1995 | Berndt ................... C12M 41/46 |
| | | 356/442 |
| 8,873,027 B2 * | 10/2014 | Sugiyama ............. G06T 7/0012 |
| | | 435/288.7 |

(Continued)

FOREIGN PATENT DOCUMENTS

| CN | 105450910 A | 3/2016 |
| JP | 2005-295818 A | 10/2005 |

OTHER PUBLICATIONS

Office Action issued in Chinese Patent Application No. 201710556445.1 dated Aug. 1, 2019, consisting of 21 pp. (English Translation Provided).

*Primary Examiner* — Eric Rush
(74) *Attorney, Agent, or Firm* — Volpe and Koenig, P.C.

(57) ABSTRACT

An observation apparatus includes an imaging unit, a driving mechanism, and a control section. The imaging unit includes an imaging section and an illumination section. The imaging section includes an image sensor and an imaging optical system, and images a sample to output an image signal. The illumination section includes a plurality of emitting sections which are located away from an optical axis of the imaging optical system and configured to emit illumination light toward the sample. The driving mechanism moves the imaging unit. The control section controls operations of the imaging section, the illumination section, and the driving mechanism. The control section determines a lighting emitting section of the emitting sections and causes the lighting emitting section to light based on the image signal, when the imaging unit is moved by the driving mechanism.

17 Claims, 13 Drawing Sheets

(51) Int. Cl.
*G06K 9/20* (2006.01)
*G02B 21/00* (2006.01)
*H04N 5/374* (2011.01)

(52) U.S. Cl.
CPC ............. *G06K 9/20* (2013.01); *H04N 5/3741* (2013.01); *G06T 2207/30024* (2013.01)

(58) Field of Classification Search
CPC .. G06K 7/10; G06K 7/10544; G06K 7/10554; G06K 7/10594; G06K 7/10603; G06K 7/10683; G06K 7/10693; G06K 7/10712; G06K 7/10722; G06K 7/10762; G06T 7/0002; G06T 7/0004; G06T 7/0012; G06T 2207/30004; G06T 2207/30024; G06T 2207/30072; H04N 3/00; H04N 3/02; H04N 3/04; H04N 3/06; H04N 3/14; H04N 3/15; H04N 3/1506; H04N 3/1587; H04N 3/1593; H04N 3/28; H04N 5/247; H04N 5/3741; H04N 1/00519; H04N 5/2256; G02B 7/02; G02B 7/021; G02B 21/0032; G02B 21/0036; G02B 21/0044; G02B 21/32; G02B 21/34; G02B 21/36; G02B 21/361; G02B 21/362; G02B 21/365; G01N 15/02; G01N 15/0205; G01N 15/0227; C12M 1/00; C12M 1/34; C12M 1/3407; C12M 1/3446; C12M 41/00; C12M 41/36; C12M 41/46; C12M 41/48
USPC ....... 382/100, 108, 110, 128, 129, 133, 134, 382/141, 144–148, 151–153, 312, 315, 382/317–319, 321–325; 348/79, 80, 348/86–90, 94, 95, 206, 211.11, 262; 435/287.3, 288.7, 808; 422/63, 82.05; 250/206, 206.1, 206.2, 206.3, 208.1; 356/222
See application file for complete search history.

(56) References Cited

U.S. PATENT DOCUMENTS

| | | | | |
|---|---|---|---|---|
| 9,025,246 | B2* | 5/2015 | Oda | G02B 21/084 |
| | | | | 359/368 |
| 2004/0256571 | A1* | 12/2004 | Muraki | G01N 21/6458 |
| | | | | 250/458.1 |
| 2008/0279441 | A1* | 11/2008 | Matsuo | G06T 7/0012 |
| | | | | 382/133 |
| 2009/0080611 | A1* | 3/2009 | Ganz | G01N 21/255 |
| | | | | 378/73 |
| 2009/0296203 | A1* | 12/2009 | Kojima | G02B 21/365 |
| | | | | 359/363 |
| 2012/0081532 | A1* | 4/2012 | Kumai | A61B 1/042 |
| | | | | 348/77 |
| 2012/0114218 | A1* | 5/2012 | Atkin | C12M 41/36 |
| | | | | 382/133 |
| 2012/0275681 | A1* | 11/2012 | Honda | C12M 41/36 |
| | | | | 382/133 |
| 2013/0038727 | A1* | 2/2013 | Clark | C12M 41/14 |
| | | | | 348/143 |
| 2013/0088221 | A1* | 4/2013 | Van Zon | G01N 15/0656 |
| | | | | 324/228 |
| 2013/0123985 | A1* | 5/2013 | Hirai | G01N 21/21 |
| | | | | 700/259 |
| 2013/0309710 | A1* | 11/2013 | Nakamura | C12Q 1/02 |
| | | | | 435/29 |
| 2014/0133702 | A1* | 5/2014 | Zheng | G06K 9/00624 |
| | | | | 382/103 |
| 2014/0273188 | A1* | 9/2014 | Mohan | G02B 21/0076 |
| | | | | 435/287.2 |
| 2015/0241683 | A1* | 8/2015 | Oba | G06T 7/0004 |
| | | | | 348/79 |

* cited by examiner

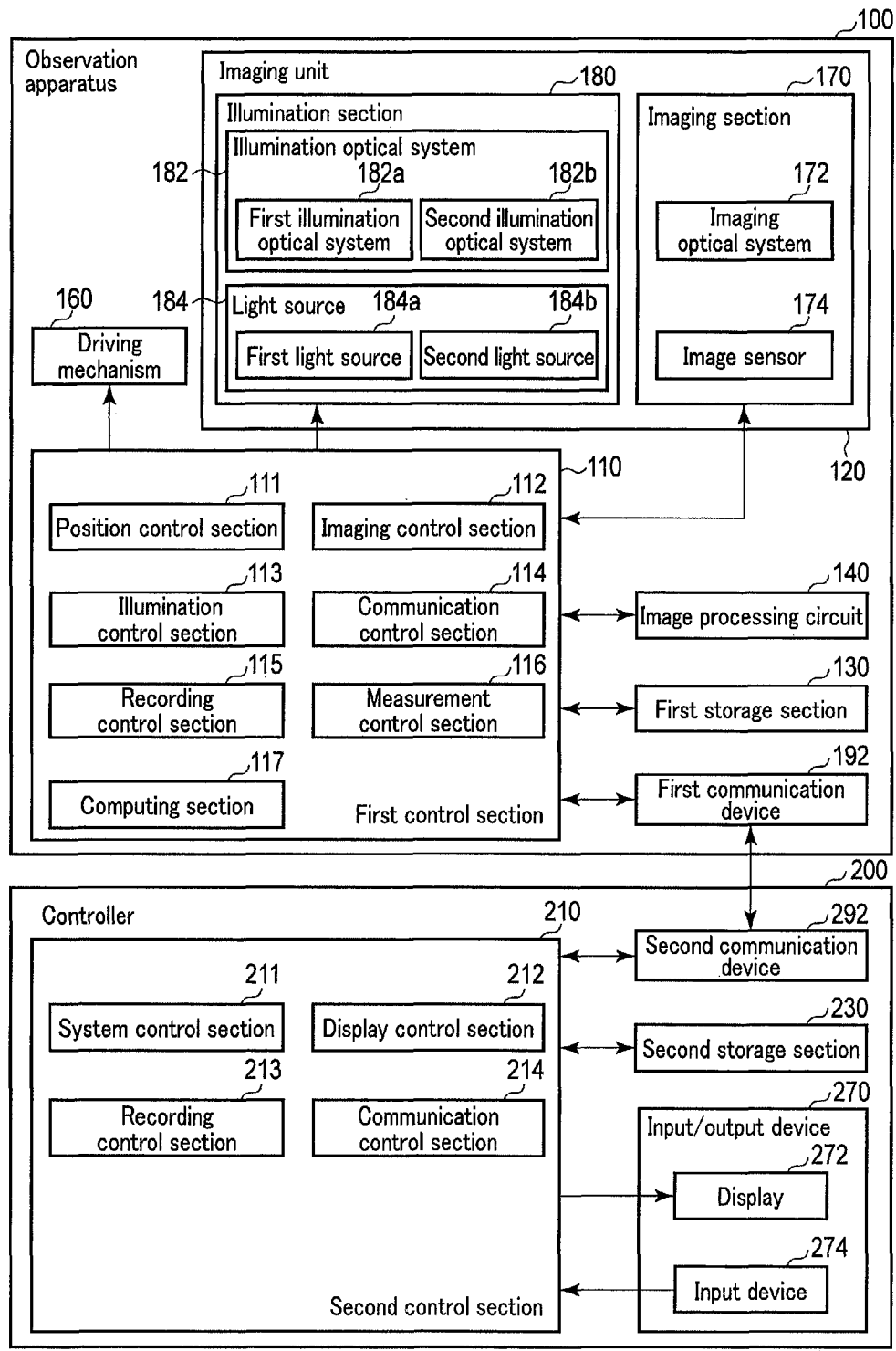
F I G. 2

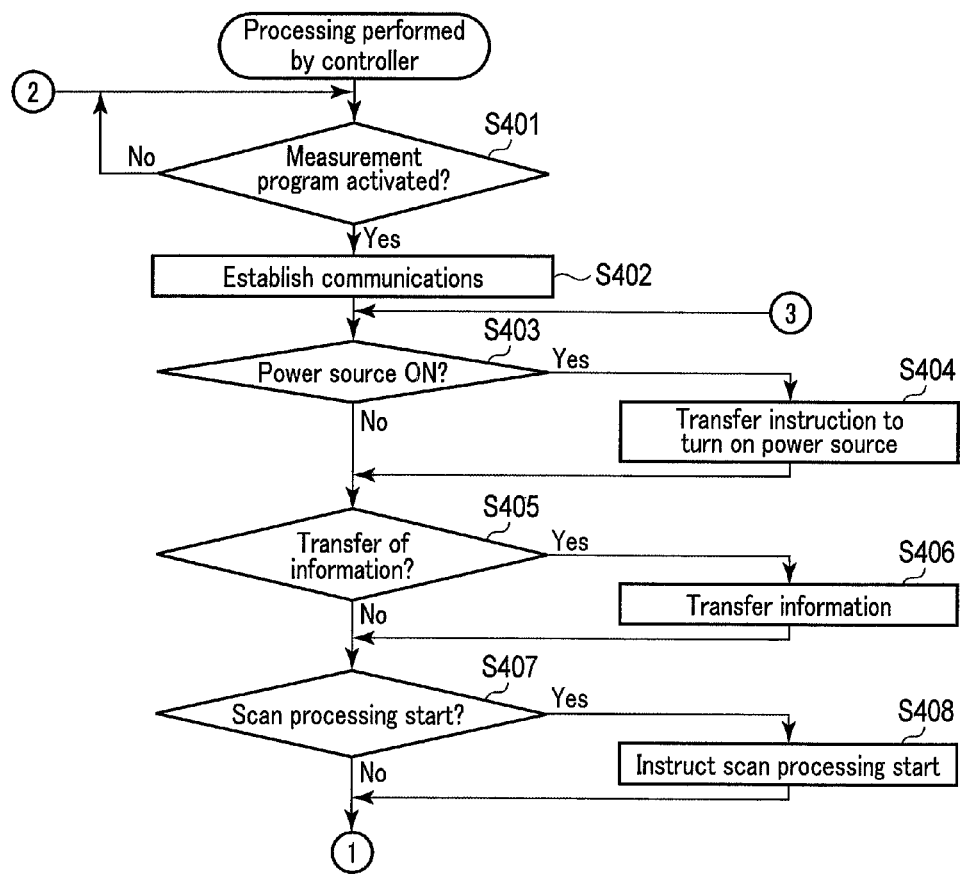
F I G. 11A

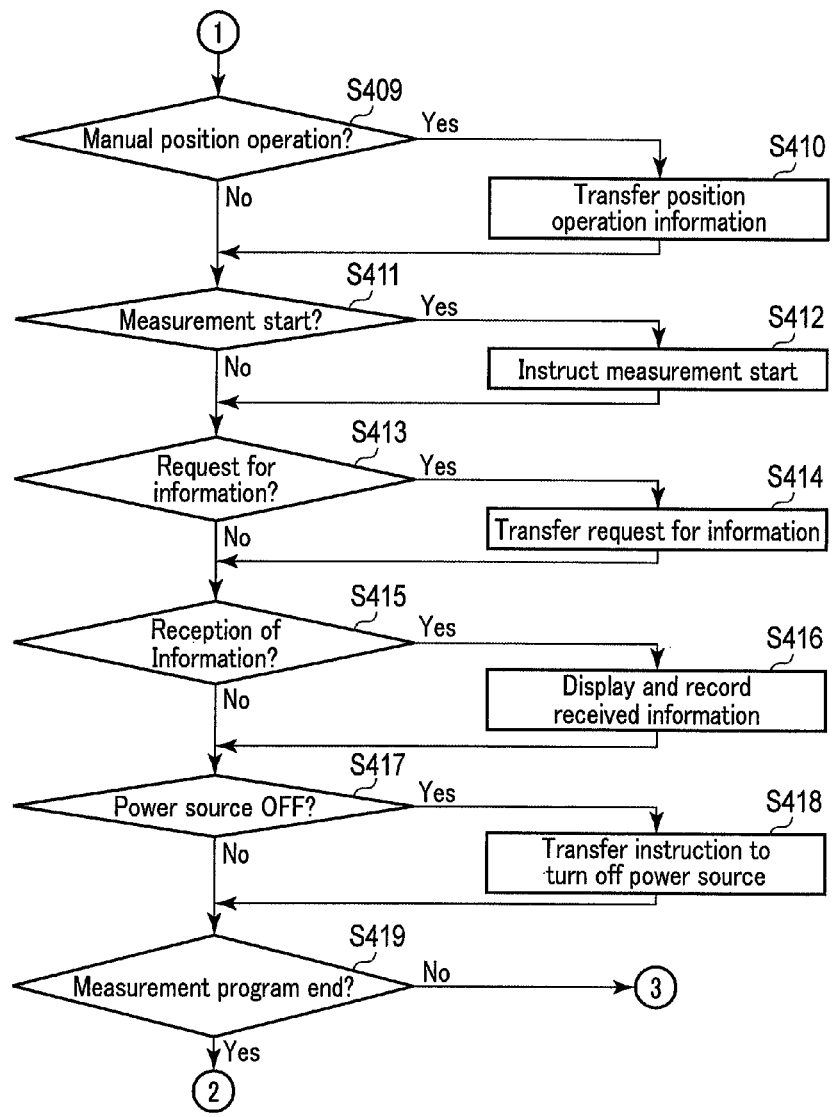
F I G. 11B

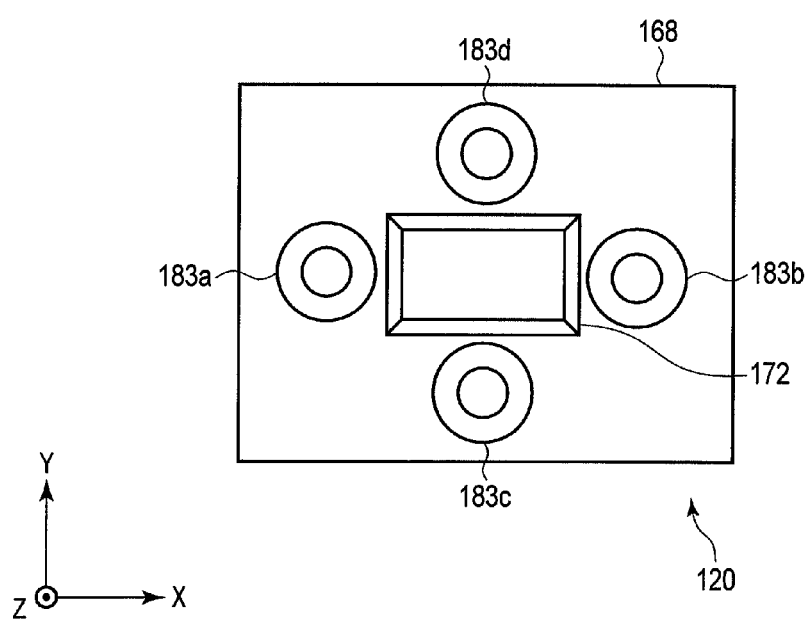
F I G. 12

OBSERVATION APPARATUS, METHOD FOR CONTROLLING OBSERVATION APPARATUS, AND NON-TRANSITORY COMPUTER-READABLE MEDIUM STORING CONTROL PROGRAM FOR OBSERVATION APPARATUS

CROSS-REFERENCE TO RELATED APPLICATIONS

This application is based upon and claiming the benefit of priority from prior Japanese Patent Application No. 2016-137117, filed Jul. 11, 2016, the entire contents of which are incorporated herein by reference.

BACKGROUND OF THE INVENTION

1. Field of the Invention

The present invention relates to an observation apparatus, a method for controlling an observation apparatus, and a non-transitory computer-readable medium storing a control program for the observation apparatus.

2. Description of the Related Art

In general, an apparatus wherein a culture vessel is statically placed in an incubator and images of cultured cells or the like in the culture vessel are taken, is known in the art. For example, Japanese Patent Application KOKAI Publication No. 2005-295818 discloses a technique related to an apparatus which takes a number of images while moving a camera (imaging section) inside an incubator so as to take images of cells existing in a wide range of a culture vessel.

BRIEF SUMMARY OF THE INVENTION

According to an aspect of the invention, an observation apparatus includes an imaging unit including an imaging section that includes an image sensor and an imaging optical system, and that images a sample to output an image signal, and an illumination section that includes a plurality of emitting sections which are located away from an optical axis of the imaging optical system and configured to emit illumination light toward the sample, a driving mechanism that moves the imaging unit, and a control section that controls operations of the imaging section, the illumination section, and the driving mechanism, wherein the control section determines a lighting emitting section of the emitting sections and causes the lighting emitting section to light based on the image signal, when the imaging unit is moved by the driving mechanism.

According to an aspect of the invention, a method for controlling an observation apparatus includes causing an imaging section including an image sensor and an imaging optical system to image a sample, causing the imaging section to output an image signal acquired by imaging, in an illumination section that includes emitting sections located away from an optical axis of the imaging optical system, determining a lighting emitting section of the emitting sections, causing the lighting emitting section to light based on the determination to illuminate the sample, and causing a driving mechanism to move an imaging unit including the imaging section and the illumination section, wherein the determining is carried out based on the image signal, when the imaging unit is moved by the driving mechanism.

According to an aspect of the invention, a non-transitory computer-readable medium stores a control program for an observation apparatus to cause a computer to execute causing an imaging section including an image sensor and an imaging optical system to image a sample, causing the imaging section to output an image signal acquired by imaging, in an illumination section that includes emitting sections located away from an optical axis of the imaging optical system, determining a lighting emitting section of the emitting sections, causing the lighting emitting section to light based on the determination to illuminate the sample, and causing a driving mechanism to move an imaging unit including the imaging section and the illumination section, wherein the determining is carried out based on the image signal, when the imaging unit is moved by the driving mechanism.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute, a part of the specification, illustrate embodiments of the invention, and together with the general description given above and the detailed description of the embodiments given below, serve to explain the principles of the invention.

FIG. 2 is a block diagram showing an outline of a configuration example of the measurement system according to the first embodiment.

FIG. 11A is a flowchart illustrating an example of processing performed by a controller according to the first embodiment.

FIG. 11B is a flowchart illustrating an example of processing performed by a controller according to the first embodiment.

FIG. 12 is a view showing an outline of a configuration example of an imaging unit according to a second embodiment.

DETAILED DESCRIPTION OF THE INVENTION

First Embodiment

The first embodiment of the present invention will be explained with reference to the drawings. A measurement system of this embodiment is a system which takes images of a cell, a cell group, and a tissue which are being cultured, and which makes a record of the numbers of cells or cell groups and the morphology thereof. The technique of this embodiment realizes a measurement system configured to detect a vessel edge or the like to be observed and to perform imaging under appropriate illumination control based on the detection. The imaging may be a photography. The acquired image may be either a still image or a moving image.

Configuration of Measurement System

Figure 1:
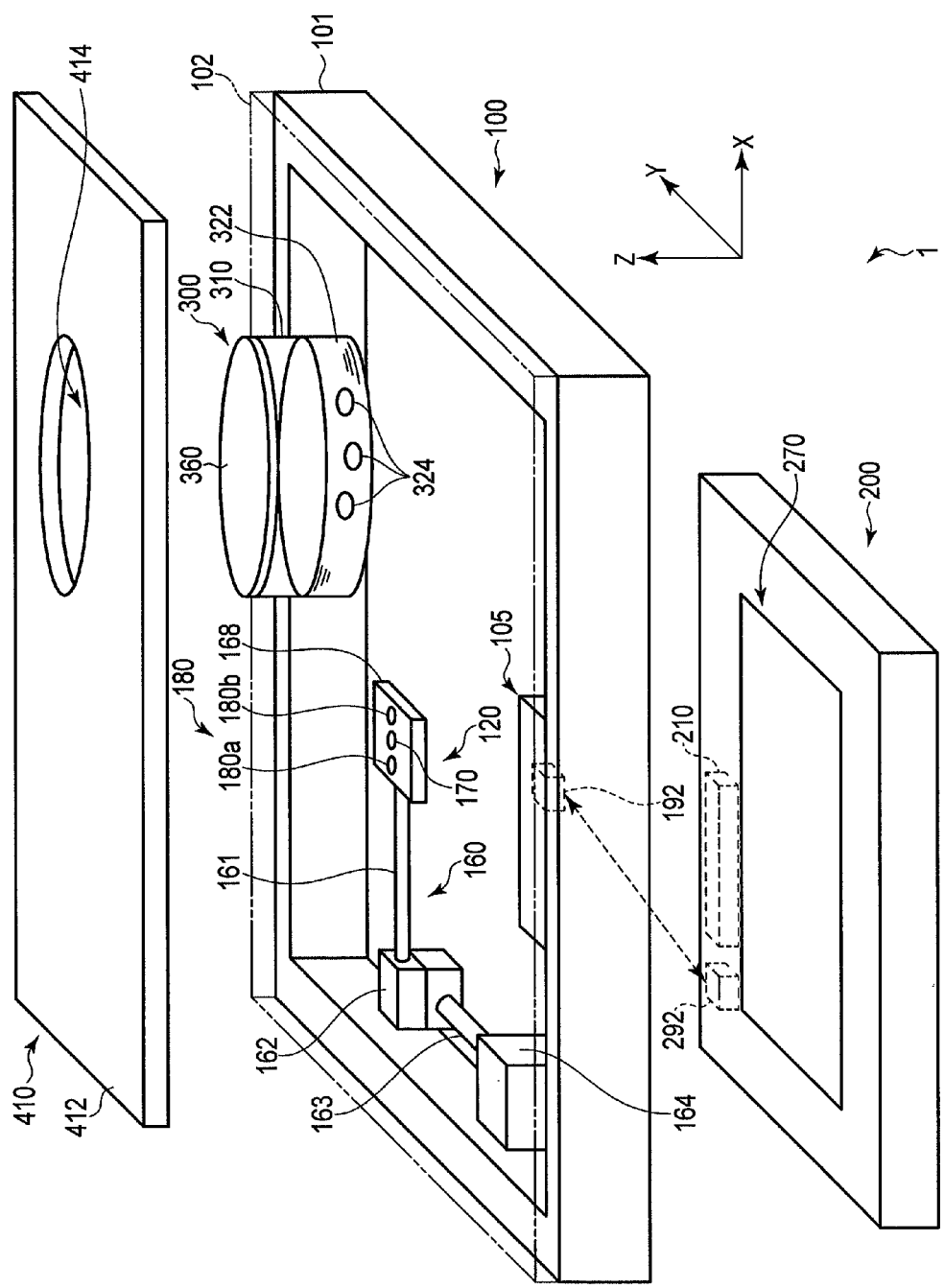
FIG. 1 is a schematic view illustrating an outline of the appearance of a measurement system according to a first embodiment.

FIG. 1 is a schematic view illustrating an outline of the appearance of a measurement system. FIG. 2 is a block diagram illustrating a configuration example of the measurement system 1. The measurement system 1 includes an observation apparatus 100 and a controller 200. As shown in FIG. 1, the observation apparatus 100 is approximately plate-shaped. The observation apparatus 100 is provided, for example, inside an incubator, and a sample 300 to be observed is arranged on top of the observation apparatus 100. For the sake of explanation, an x-axis and a y-axis perpendicular to each other are defined in a plane parallel to the surface on which the sample 300 is arranged, and a z-axis is defined as an axis perpendicular to both the x-axis and the y-axis. A transparent plate 102 is placed as a top plate of the observation apparatus 100, and an imaging section 170 is provided inside a casing 101 of the observation apparatus 100. The observation apparatus 100 takes an image of the sample 300, via the transparent plate 102 interposed, and the image of the sample 300 is acquired thereby. On the other hand, the controller 200 is provided, for example, on the outside of the incubator. The observation apparatus 100 and the controller 200 communicate with each other. The controller 200 controls operations of the observation apparatus 100.

(Sample)

An example of the sample 300 to be observed by the measurement system 1 will be described below. A culture medium 322 is in a vessel 310, and cells 324 are cultured in the culture medium 322. The vessel 310 may be, for example, a petri dish, a culture flask, a multiwell plate, or the like. The vessel 310 is a culture vessel for culturing a biological samples, for example. The vessel 310 is not limited to any specific shape or size. The vessel 310 is, for example, a transparent vessel having a surface or part that is transparent to illumination light. The culture medium 322 may be either a liquid medium or a solid medium. The cells 324 to be measured may be either adhesive cells or floating cells. Alternatively, the cells 324 may be spheroids or tissues. In addition, the cells 324 may be derived from any organism or may be bacteria or the like. As described above, the sample 300 includes a living sample which is either the living substance itself or is derived from the living substance.

(Observation Apparatus)

As shown in FIG. 1, the transparent plate 102 made of, for example, glass, is provided on top of the casing 101 of the observation apparatus 100. The sample 300 is statically placed on this transparent plate 102. Although FIG. 1 shows that the top plate of the casing 101 is entirely transparent, the observation apparatus 100 may be designed so that part of the top plate of the casing 101 is a transparent plate, and the remaining part of the top plate is opaque.

The transparent plate 102 may be overlaid with a fixing frame 410 to determine the position where the sample 300 is placed on the transparent plate 102 and to fix the sample 300. The fixing frame 410 may be designed so that it is arranged at a specific position with respect to the transparent plate 102. For example, the fixing frame 410 may have the same size as the transparent plate 102. The fixing frame 410 includes a fixing plate 412 and a hole 414 formed in the fixing plate 412. The hole 414 has a diameter slightly larger than the outer diameter of the vessel 310 of the sample 300. Therefore, in the state where the fixing frame 410 is placed on the transparent plate 102, the vessel 310 can be fixed in the hole 414. A plurality of fixing frames 410 of different types may be prepared in accordance with the types of vessels 310 of the sample 300. The fixing frame 410 may be employed; alternatively, it can be omitted.

Various structural elements of the observation apparatus 100 are provided inside the casing 101. The interior of the incubator has a temperature of 37° C. and a humidity of 95%. Since the observation apparatus 100 is used in an environment of high ambient temperature and humidity, the casing 101 and the transparent plate 102 are designed to maintain airtightness. To protect the interior of the observation apparatus 100 from high-humidity environment, the inside enclosed by the casing 101 and the transparent plate 102 may have a higher pressure in comparison with the outside thereof.

An imaging unit 120 is provided inside the casing 101. As shown in FIG. 1 and FIG. 2, the imaging unit 120 includes a support section 168, the imaging section 170, and an illumination section 180. The imaging section 170 includes an imaging optical system 172 and an image sensor 174. The imaging section 170 takes an image of the region where the sample 300 is present, and thus acquires an image of the sample 300. The imaging section 170 generates image data based on an image which is formed on the imaging plane of the image sensor 174 by the imaging optical system 172. The imaging optical system 172 is preferably a zoom optical system capable of changing its focal distance.

As shown in FIG. 1, the illumination section 180 is provided near or around the imaging section 170 on both sides of the imaging section 170 in the support section 168. The illumination section 180 emits illumination light in the direction toward the transparent plate 102, namely, in the direction toward the sample 300. If the illumination section 180 includes a plurality of light sources or illumination optical systems, the light sources or illumination optical systems are preferably arranged, but is not limited, to be symmetrical with respect to the image sensor 174 of the imaging section 170. The light sources may also be called the light emitting elements. In this embodiment, the illumination section 180 includes a first illumination section 180a and a second illumination section 180b. As shown in FIG. 2, the illumination section 180 includes an illumination optical system 182 and a light source 184. The illumination optical system 182 includes a first illumination optical system 182a and a second illumination optical system 182b. The light source 184 includes a first light source 184a and a second light source 184b. The illumination light emitted from the first light source 184a illuminates the sample 300 through the first illumination optical system 182a. Similarly, the illumination light emitted from the second light source 184b illuminates the sample 300 through the second illumination optical system 182b.

Thus, the illumination section 180 includes a plurality of emitting sections that are arranged around the imaging section 170 and emit illumination light. For example, the first illumination section 180a and the second illumination section 180b emit illumination light respectively from a first emitting section 183a and a second emitting section 183b. As described above, the emitting sections, which emit illumination light may be, for example, light sources that emit illumination light, or illumination optical systems that emit illumination light. Furthermore, switching from a state in which the first illumination optical system 182a emits illumination light to a state in which the second illumination optical system 182b emits illumination light can be represented as switching the emitting section emitting the illumination light from the first illumination optical system 182a to the second illumination optical system 182b. That can also be represented as switching from a state in which the first emitting section 183a emits illumination light to a state in which the second emitting section 183b emits illumination light.

The illumination section 180 of the embodiment includes two illumination optical systems and two light sources; however, the number of illumination optical systems and light sources is not limited to two. For example, the number of illumination optical systems and light sources of the illumination section 180 may be more than two, and the numbers of illumination optical systems and the number of light sources may be different. Although the illumination section 180 is described as being arranged in the support section 168, what is required in practice is merely that the emitting sections of the respective illumination optical systems that emit illumination light is arranged in the support section 168. For example, the light sources may be arranged at any positions in the observation apparatus 100. A plurality of illumination optical systems having a common light source may be arranged in the support section 168. In this case, an optical system to switch the illumination optical systems that emit illumination light is provided. Thus, the imaging unit 120 includes at least the imaging optical system 172 and the illumination optical system 182, but do not necessarily include the image sensor 174 and the light source 184.

In this embodiment, to avoid or reduce any damage to the cells 324 by illumination light, the light source 184 is described as, but is not limited to, a red light-emitting diode (red LED) as an example. The light source 184 may be a red light source configured to emit red light, for example, by using a fluorescent lamp or a mercury lamp. The wavelength of illumination light emitted by the light source 184 may fall within any of ultraviolet, visible, and infrared wavelength regions, depending on an object to be observed and an environment inside the incubator. Furthermore, each of the light sources may comprise a cooling mechanism. In the following, the description with only the term "illumination light" represents a case in which the illumination light may be emitted from any of the illumination optical systems, any of the red light sources, and any combination of the illumination optical systems and red light sources. Furthermore, the description with only the term "emitting section" represents a case in which the emitting section may be any of the plurality of emitting sections.

Referring back to FIG. 1, explanations will be continued. The imaging unit 120 is moved by a driving mechanism 160. The driving mechanism 160 is provided with an X feed screw 161 and an X actuator 162 for moving the imaging unit 120 in the X-axis direction. The driving mechanism 160 is also provided with a Y feed screw 163 and a Y actuator 164 for moving the imaging unit 120 in the Y-axis direction. The imaging section 170 can partly acquire an image of the sample 300 on the transparent plate 102 only on a one-by-one basis. However, by moving the imaging unit 120 with the driving mechanism 160, the imaging section 170 can acquire an image of a wide range.

The imaging position in the Z-axis direction is changed by changing the focus position of the imaging optical system 172 in an optical axis direction. In other words, the imaging optical system 172 is provided with a focus adjustment mechanism for moving a focusing lens in the optical axis direction. In place of the focus adjustment mechanism or in combination therewith, the driving mechanism 160 may be provided with a Z feed screw and a Z actuator for moving the imaging unit 120 in the Z-axis direction.

In this embodiment, an X-Y plane is defined in a plane parallel to the surface on which the sample 300 is arranged, as described above. For the purpose of explanation in the following, the positive direction of the X-axis direction is referred to as an X+ direction, and defined as a direction away from the X actuator 162 along the longitudinal direction of the X feed screw 161. Similarly, the positive direction of the Y-axis direction is referred to as a Y+ direction, and defined as a direction away from the Y actuator 164 along the longitudinal direction of the Y feed screw 163. The positive direction of the Z-axis direction is referred to as a Z+ direction, and defined as a direction from the imaging unit 120 toward the sample 300. Furthermore, the negative direction of the X-axis direction, the negative direction of the Y-axis direction, and the negative direction of the Z-axis direction are respectively referred to as an X− direction, a Y− direction, and a Z− direction.

In this embodiment, the imaging optical system 172 and the emitting sections are described as being arranged on a side of the imaging unit 120 facing the sample 300, that is, a surface on the side of the Z+ direction. However, the imaging optical system 172 and the emitting sections are not limited to this arrangement. The imaging optical system 172 and the emitting sections may be arranged to sandwich the sample 300 in the Z direction; for example, the imaging optical system 172 may be arranged on the side of the Z− direction of the sample 300 and a plurality of emitting sections may be arranged on the side of the Z+ direction of the sample 300. Advantages of the embodiment described below will be obtained even if such an arrangement is employed. In this embodiment, the first emitting section 183a is provided on a side of the X− direction of the imaging unit 120 and the second emitting section 183b is provided on a side of the X+ direction thereof.

A circuit group 105 for controlling the respective operations of the driving mechanism 160, the imaging section 170 and the illumination section 180 is provided inside the casing 101. A first communication device 192 is provided for the circuit group 105. The first communication device 192 is, for example, a device which communicates wirelessly with the controller 200. For example, wireless communications, such as Wi-Fi or Bluetooth are utilized for the communications. The observation apparatus 100 and the controller 200 may be connected by a wire, and wired communications may be carried out. As described above, the imaging section 170 that generates image data by imaging via the transparent plate 102 and the driving mechanism 160 that moves the imaging section 170 are provided inside the casing 101. Accordingly, the structure of the apparatus can be reliable, easy to handle and clean, and can prevent contamination or the like.

As shown in FIG. 2, the observation apparatus 100 includes a first control section 110, a first storage section 130, and an image processing circuit 140, in addition to the driving mechanism 160, the imaging unit 120, and the first communication device 192 described above. The first control section 110, the first storage section 130, the image processing circuit 140, and the first communication device 192 are arranged, for example, in the circuit group 105 described above.

The first control section 110 controls operations of each of the elements of the observation apparatus 100. The first control section 110 functions as a position control section 111, an imaging control section 112, an illumination control section 113, a communication control section 114, a recording control section 115, a measurement control section 116, and an computing section 117. The position control section 111 controls the driving mechanism 160 to control the position of the imaging unit 120. The position control section 111 acquires a position of the imaging unit 120 which is moved by the driving mechanism 160. The imaging control section 112 controls operations of the imaging section 170 to cause the imaging section 170 to acquire an image of the sample 300. The illumination control section 113 controls the illumination section 180. The communication control section 114 controls the communications with the controller 200, which are performed by using the first communication device 192. The recording control section 115 controls the recording of data obtained by the observation apparatus 100. The measurement control section 116 controls the overall measurement, including measurement timing and the number of times the measurement is performed. The computing section 117 performs various analyses based on the image acquired by the imaging section 170, a brightness value, etc.

The first storage section 130 stores, for example, programs and various parameters for use in the first control section 110. The first storage section 130 also stores data obtained by the observation apparatus 100.

The image processing circuit 140 performs various kinds of image processing for the image data generated by the imaging section 170. After the image processing by the image processing circuit 140, data is, for example, stored in the first storage section 130 or transferred to the controller 200 by way of the first communication device 192. The first control section 110 or the image processing circuit 140 may perform various kinds of analysis, based on the obtained image. For example, the first control section 110 or the image processing circuit 140 extracts an image of a cell or cell group included in the sample 300, counts the number of cells or cell groups, or calculates a shape or size thereof, based on the obtained image. The results of the analysis thus obtained are, for example, stored in the first storage section 130 or transferred to the controller 200 by way of the first communication device 192. The processing performed by the image processing circuit 140 may be performed by the computing section 117.

Figure 3:
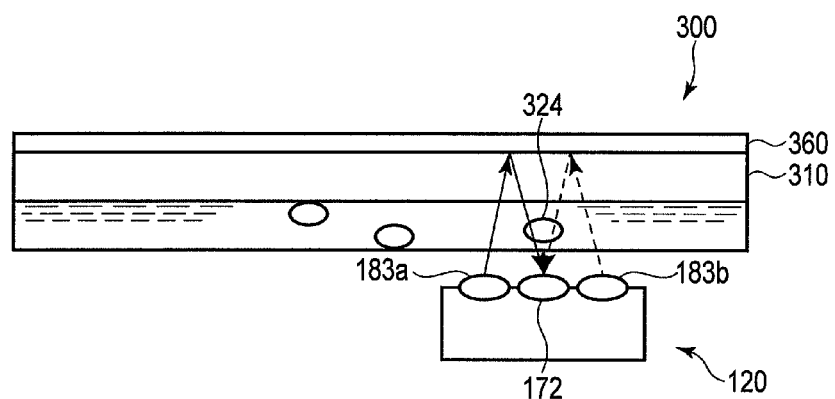
FIG. 3 is a side view showing an outline of a configuration example of a periphery of a sample according to the first embodiment.

FIG. 3 is a schematic side view of the sample 300 and the imaging unit 120. As shown in FIG. 3, a vessel top plate 360 is on top of the sample 300. The vessel top plate 360 reflects part of illumination light. As indicated by solid arrows in FIG. 3, for example, illumination light emitted from the first emitting section 183a of the illumination section 180 irradiates the vessel top plate 360. Part of the illumination light is reflected by the vessel top plate 360 and part of the illumination light is transmitted through the vessel top plate 360. Part of reflected light illuminates the cell 324 and enters the imaging optical system 172 of the imaging section 170. Thus, the reflected light entering the imaging optical system 172 includes transmitted light transmitted through the cell 324. Illumination light emitted from the second emitting section 183b indicated by dashed arrows in FIG. 3 also illuminates the cell 324 and enters the imaging optical system 172, in the same manner as described above. As shown in FIG. 3, in this embodiment, the emitting section is located away from the optical axis of the imaging optical system 172.

The imaging section 170 acquires and images the light that has entered in the imaging optical system 172, as described above. Image acquisition by the imaging section 170 will be explained with reference to the schematic view shown in FIG. 4. The observation apparatus 100 repeatedly takes an image, while changing its position in the X direction and the Y direction, for example, in a first plane, and a plurality of images are acquired thereby. The image processing circuit 140 synthesizes these images, thereby preparing one first image 611 of the first plane. The first plane is, for example, a plane perpendicular to the optical axis of the imaging section 170, that is, a plane parallel to the transparent plate 102. Also, the observation apparatus 100 changes the imaging position in the thickness direction to a second plane and to a third plane, and repeatedly takes an image, while changing its position in the X direction and Y direction in each of the planes. The images are synthesized, so that a second image 612 and a third image 613 are acquired. The thickness direction is the Z-axis direction, namely, the optical axis direction of the imaging section 170, and is perpendicular to the transparent plate 102. In this manner, an image at each three-dimensional position is acquired.

In the above, a description is given of an example in which an image is repeatedly taken, with the imaging plane being changed in the Z direction. Instead, an image may be repeatedly taken, with the imaging plane being changed only in the X direction and the Y direction without obtaining a plurality of images in the Z direction. In this case, a synthesis image of one plane is obtained. In the method for acquiring the first image 611, the second image 612 and the third image 613, a scan may be performed in the X direction and Y direction, with the position in the Z-axis direction being kept fixed, and after changing the position in the Z-axis direction, a scan may be performed in the X direction and Y direction. Alternatively, an image of a given position in the X direction and Y direction may be taken a number of times, with the position being changed in the Z-axis direction, and this operation may be performed, with the scan position being changed in the X direction and Y direction.

In imaging for measurement, the sample 300 need not be continuously irradiated with illumination light. The sample 300 may be irradiated with illumination light only at the instant of imaging. Due to the shortened irradiation time, the damage to the cell 324 can be reduced. Thus, the sample 300 can be irradiated with illumination light of sufficient intensity at the timing of imaging. This matter contributes to obtaining a quality image.

As described above, the imaging section 170 repeatedly takes an image, while changing its position in the X direction and the Y direction, thereby acquiring a plurality of images. An example of illumination control at this time will be explained with reference to the schematic view shown in FIGS. 5A, 5B, and 5C. Explanations will be given for a case in which the imaging unit 120 repeatedly takes an image, while changing its position in the X- direction. The relative position of the imaging unit 120 with respect to the sample 300 may be changed by movement of the imaging unit 120 by the driving mechanism 160. In the following, a case in which the first emitting section 183a, that is, one emitting section emits illumination light will be described. However, the technique of this embodiment is not limited to this case. For example, when the first emitting section 183a emits illumination light, the second emitting section 183b may supplementarily emit illumination light.

Figure 5A:
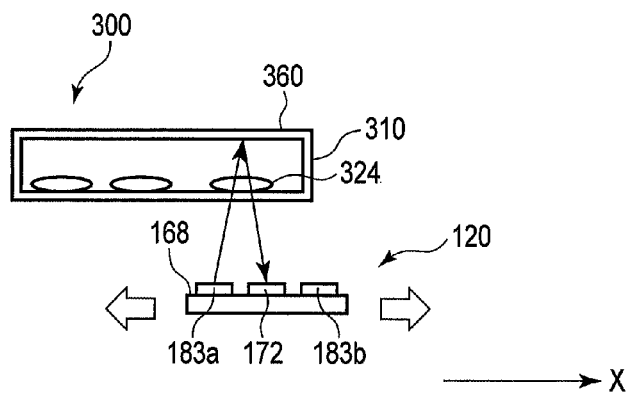
FIG. 5A is a view for explaining illumination control at a time of image acquisition by an imaging unit according to the first embodiment.

In a state shown in FIG. 5A, the sample 300 is illuminated with illumination light emitted by the first emitting section 183a arranged in a direction of a forward movement side of the imaging unit 120. As described above, the illumination light emitted by the first emitting section 183a is reflected by the vessel top plate 360 and illuminates the cell 324. The imaging section 170 receives and images the illumination light that illuminated the cell 324.

Figure 5B:
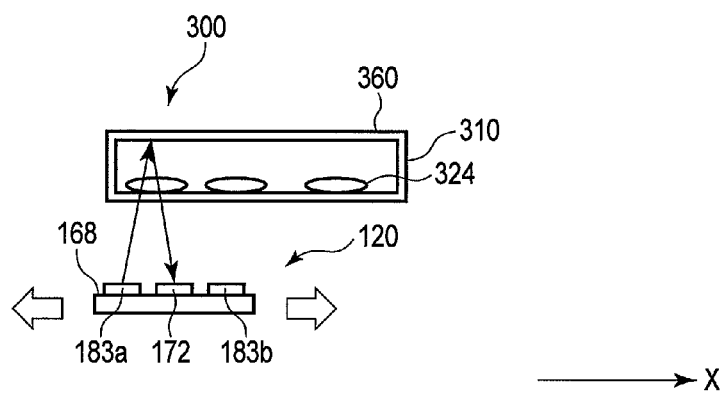
FIG. 5B is a view for explaining illumination control at a time of image acquisition by an imaging unit according to the first embodiment.

In FIG. 5B, a state represents that the imaging unit 120 has moved from the state shown in FIG. 5A in the X- direction. In the state shown in FIG. 5B, the imaging unit 120 is still located under the sample 300, and the imaging section 170 can receive the illumination light emitted by the first emitting section 183a via the vessel top plate 360 in the same manner as in the case of the state shown in FIG. 5A.

Figure 5C:
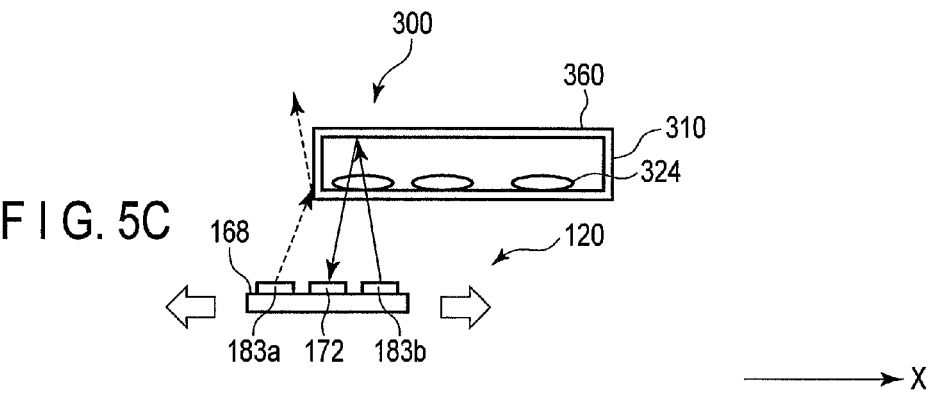
FIG. 5C is a view for explaining illumination control at a time of image acquisition by an imaging unit according to the first embodiment.

In FIG. 5C, a state represents that the imaging unit 120 has further moved from the state shown in FIG. 5B in the X-direction. In the state shown in FIG. 5C, the illumination light emitted by the first emitting section 183a mostly scatters as indicated by the dashed arrows in FIG. 5C, for example, at an edge portion of the vessel 310 that falls within the optical path, without being incident on the vessel top plate 360. Therefore, the imaging section 170 cannot sufficiently receive the illumination light. In this case, the amount of light received by the imaging section 170 is reduced. When the first control section 110 detects a change in brightness value or light intensity that occurs as the illumination light scatters at the edge portion of the vessel as described above, it determines that the imaging unit 120 reaches the edge portion of the vessel 310. At this time, the illumination control section 113 switches the emitting section that emits illumination light from the first emitting section 183a to the second emitting section 183b. After the switching, the illumination light emitted by the second emitting section 183b can be incident on the vessel top plate 360 as indicated by the solid arrows in the state shown in FIG. 5C, and the reflected light and the transmitted light transmitted through the cell 324 of the reflected light can be incident on the imaging optical system 172. In this embodiment, the emitting section of the imaging unit 120 is located away from the optical axis of the imaging optical system 172. If the illumination light emitted by the emitting section scatters at the edge portion of the vessel, the amount of light received by the image sensor 174 is insufficient and acquisition of an appropriate image is difficult in or near the edge portion of the vessel. In such a time, the first control section 110 switches between the emitting sections that emit illumination light, thereby reconstructing an appropriate illumination environment. Furthermore, reconstructing an appropriate illumination environment by switching between the emitting sections, can at the same time, reduce wasteful emission of illumination light. The technique of this embodiment contributes to not only saving of energy necessary for using the observation apparatus 100, but also to reducing the amount of heat generation. As described above, the imaging section 170 can acquire an image under appropriate illumination. An example of illumination control at the time of imaging in the imaging unit 120 has been described. Regardless of from which region and in which direction the imaging unit 120 moves, the first control section 110 switches between the emitting sections that emit illumination light upon detecting that the illumination light scatters at the edge portion of the vessel.

(Controller)

The controller 200 is, for example, a personal computer (PC) or a tablet type information terminal. In FIG. 1, a tablet type information terminal is depicted.

The controller 200 is provided with an input/output device 270 including a display 272 such as a liquid crystal display, and an input device 274 such as a touch panel. The input device 274 is not limited to the touch panel but may include a switch, a dial, a keyboard, a mouse, etc.

The controller 200 is also provided with a second communication device 292. The second communication device 292 is a device which communicates with the first communication device 192. The observation apparatus 100 and the controller 200 communicate with each other through the first communication device 192 and the second communication device 292.

The controller 200 is further provided with a second control section 210 and a second storage section 230. The second control section 210 controls operations of each of the elements of the controller 200. The second storage section 230 stores, for example, programs and various parameters for use in the second control section 210. The second storage section 230 also stores data obtained by and received from the observation apparatus 100.

The second control section 210 functions as a system control section 211, a display control section 212, a recording control section 213 and a communication control section 214. The system control section 211 performs various operations for controlling the measurement of the sample 300. The display control section 212 controls operations of the display 272. The display control section 212 causes the display 272 to display the necessary information. The recording control section 213 controls the recording of information in the second storage section 230. The communication control section 214 controls the communications with the observation apparatus 100 that are performed using the second communication device 292.

Each of the first control section 110, the image processing circuit 140, and the second control section 210 incorporates an integrated circuit such as a central processing unit (CPU), an application specific integrated circuit (ASIC), a field programmable gate array (FPGA), and a graphic processing unit (GPU). Each of the first control section 110, the image processing circuit 140, and the second control section 210 may be constituted by a single integrated circuit or by a combination of a' number of integrated circuits. The first control section 110 and the image processing circuit 140 may be made by a single integrated circuit. Each of the position control section 111, the imaging control section 112, the illumination control section 113, the communication control section 114, the recording control section 115, the measurement control section 116, and the computing section 117 of the first control section 110 may be constituted by a single integrated circuit or by a combination of a number of integrated circuits. Two or more of the position control section 111, the imaging control section 112, the illumination control section 113, the communication control section 114, the recording control section 115, the measurement control section 116, and the computing section 117 may be constituted by a single integrated circuit or the like. Likewise, each of the system control section 211, the display control section 212, the recording control section 213, and the communication control section 214 of the second control section 210 may be constituted by a single integrated circuit or by a combination of a number of integrated circuits. Two or more of the system control section 211, the display control section 212, the recording control section 213, and the communication control section 214 may be constituted by a single integrated circuit or the like. The operations of these integrated circuits are executed, for example, in accordance with programs stored in the first storage section 130 or the second storage section 230, or in accordance with the programs stored in the storage regions of the integrated circuits.

Operations of Measurement System

Figure 6:
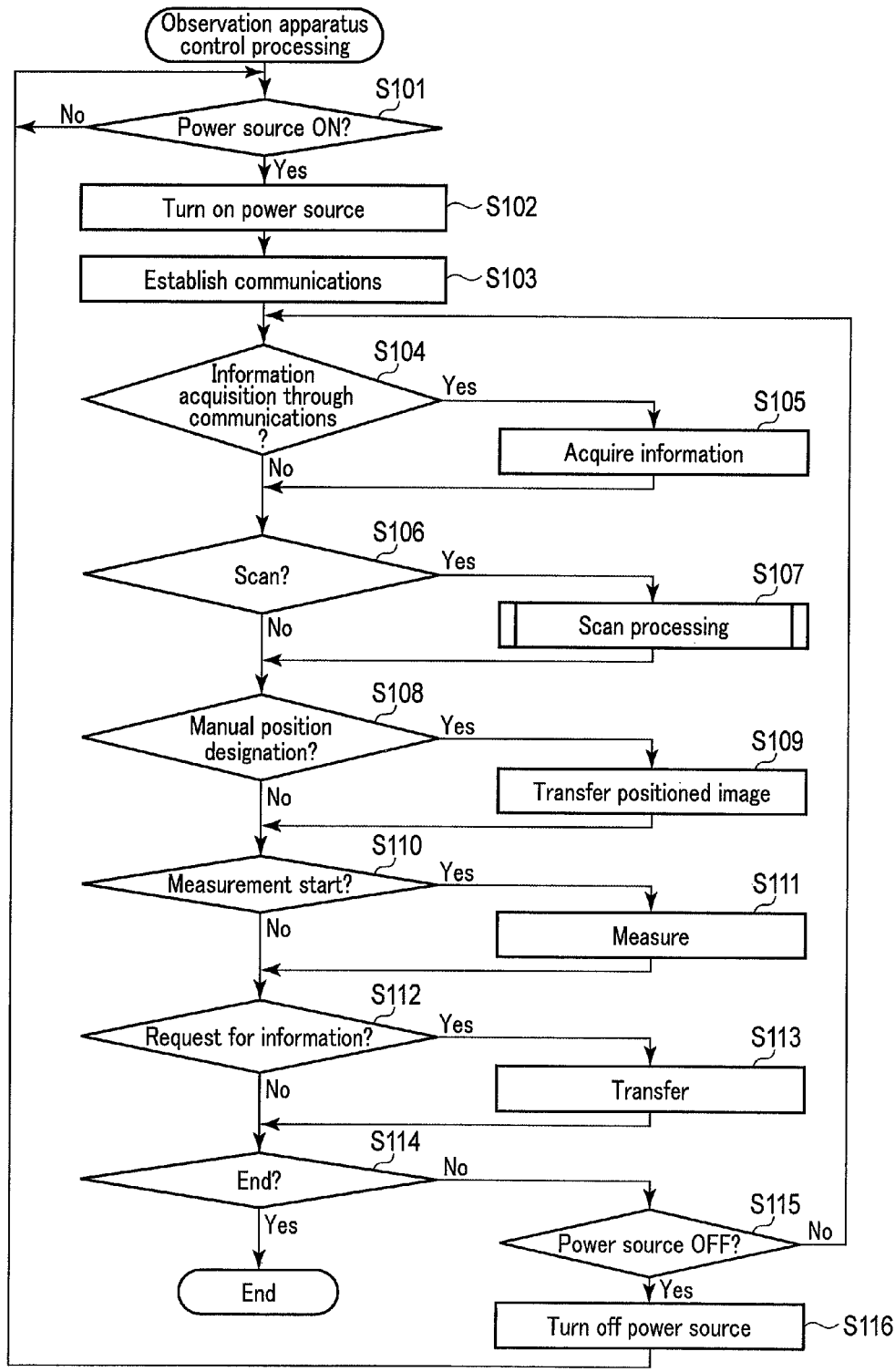
FIG. 6 is a flowchart illustrating an example of observation apparatus control processing according to the first embodiment.

Operations of the measurement system 1 will be described. First, operations of the observation apparatus 100 will be described with reference to the flowchart shown in FIG. 6. The flowchart shown in FIG. 6 starts when the observation apparatus 100, the controller 200, and the sample 300 are in place and preparations for measurement have been made.

In step S101, the first control section 110 determines whether or not the power source should be turned on. Where the power source is configured to be switched on at predetermined times and the time to switch on the power switch comes, the first control section 110 determines that the power source should be turned on. Where the observation apparatus 100 constantly communicates with the controller 200 through low-power-consumption communication means such as Bluetooth Low Energy, and when the observation apparatus 100 receives instructions to turn on the power source from the controller 200 through the communication means, it is determined that the power source should be turned on. Unless the power source is turned on, the observation apparatus control processing stands by, repeating step S101. If it is determined that the power source should be turned on, the observation apparatus control processing advances to step S102.

In step S102, the first control section 110 turns on the power source to supply power to the respective portions of the observation apparatus 100. If the power source is turned on only when the sample 300 is actually measured, power saving can be attained. In particular, if the power source of the observation apparatus 100 is a battery, advantages can be obtained, for example, the driving time of the observation apparatus 100 can be lengthened. On the other hand, the first control section 110 may determine if power consumed by operations of turning on and off the power source is greater than standby energy, for example, if imaging intervals set in the apparatus are short, to suppress power consumption as a whole.

In step S103, the first control section 110 establishes communications with the controller 200. The communication means used in the embodiment is high-speed communication means, such as Wi-Fi.

In step S104, the first control section 110 determines whether or not information should be acquired from the controller 200 through the established communications. For example, when information is transferred from the controller 200, it is determined that the information should be acquired. Unless the information is acquired, the observation apparatus control processing advances to step S106. If the information is acquired, the observation apparatus control processing advances to step S105.

In step S105, the first control section 110 acquires the information transferred from the controller 200. The acquired information includes condition information, such as measurement conditions (including imaging conditions, imaging intervals, and other parameters), a method for recording measurement results, a transfer condition for the measurement results, etc. Subsequently, the observation apparatus control processing advances to step S106.

In step S106, the first control section 110 determines whether or not a scan is to be performed. If it is determined in step S106 that the scan is not to be performed, the observation apparatus control processing advances to step S108. If it is determined that the scan is to be performed, the observation apparatus control processing advances to step S107. In step S106, the execution of the scan is determined under various conditions, for example, where the measurement by the measurement system 1 is performed for the first time, where the user designates execution of the scan, and where the current time is immediately before the start of repeatedly-executed measurement, or determined based on time intervals set by the user. The various conditions further include conditions where a portion near the vessel edge portion is to be measured and illumination control is required, for example, where the overall area of the sample 300 is to be widely measured, where a position of the edge portion of the vessel 310 is unknown, and where a measurement is to be made for a position included in the edge portion of the vessel 310.

In step S107, the first control section 110 performs scan processing. The scan processing will be described with reference to the flowchart shown in FIG. 7. In the scan processing, processing related to detect the edge portion of the vessel 310 and processing related to illumination control by the first control section 110 as described above are performed, so that the measurement system 1 can perform imaging under appropriate illumination control.

In step S201, the first control section 110 controls operations of the driving mechanism 160 so that the imaging section 170 moves to the initial position. In the following, explanations are given on the assumption that the initial position coincides with the center of the vessel 310; however, the initial position is not limited to the center of the vessel 310. For example, the first control section 110 may perform scanning first, while moving the imaging unit 120 until the edge portion of the vessel 310 is detected, to determine the vessel edge portion as the initial position. The initial position may be set by specifying the position of the vessel 310 by setting the type of vessel and designating the position where the vessel is placed, may be set by inputting coordinate data by the user, or may be set by acquiring an image by preliminary scanning and then analyzing the image. The first control section 110 acquires the amounts of movement in the X and Y directions during scanning based on outputs from the controller 200 in accordance with an input by the user or a value set in advance and stored in the first storage section 130. After the initial setting described above, the scan processing advances to step S202.

In step S202, the first control section 110 lights the second light source 184b located in the X+ direction. Here, the second light source 184b is selected as illumination. For example, the second light source 184b may be selected in accordance with starting a scan by the imaging unit 120 from the initial position toward the X+ direction. In other words, illumination located in the same direction as the scanning direction may be selected as illumination to be lit based on the set scanning direction. After the second light source 184b is lit, the scan processing advances to step S203. As described above, lighting the second light source 184b located in the X+ direction may be replaced with emitting illumination light from the second emitting section 183b located in the X+ direction. Alternatively, in step S202, the first light source 184a located in the X− direction may be lit. In other words, illumination located in the direction opposite to the scanning direction may be selected based on the scanning direction.

In step S203, the first control section 110 causes the imaging section 170 to perform imaging. At this time, the first control section 110 acquires a position of the imaging unit 120. Furthermore, the first control section 110 makes predetermined setting for the imaging optical system 172. After the imaging, the scan processing advances to step S204. For easy understanding of an overview at the sacrifice of image quality, the scan processing may be executed as below, in comparison with measurement.

In the image acquisition at the time of measurement, focal illumination, i.e., normal illumination, is used as illumination light; however, phase-contrast illumination may be used instead. The use of the focal illumination enables acquisition of an image whose outline can be easily understood even in a slightly defocused state at the time of measurement. Where the phase-contrast illumination is used, an image received in a defocused state may be an image including a number of overlapping images. This phenomenon is attributable to the fact that a plurality of light-emitting diodes (LEDs) are employed for the suppression of uneven shading. In this embodiment, during the scan time, part of the LEDs are kept lit as illumination. Therefore, even in a slightly defocused state at the time of measurement, an image enabling easy understanding of an overview can be obtained.

For example, where the imaging optical system 172 is a zoom optical system, it is set in the wide angle mode, i.e., in the mode in which the focal distance is short. In addition, the first control section 110 decreases the diameter of the aperture of the imaging optical system 172, thereby increasing the depth of field. At that time, the first control section 110 may increase the intensity of the illumination light of the illumination section 180 in accordance with the decrease in the diameter of the aperture. The first control section 110 may increase the sensitivity of the image sensor 174. For example, the sensitivity can be increased by pixel addition in which the brightness value obtained by the pixels of the image sensor 174 is added.

In step S204, the first control section 110 performs vessel edge detection processing for the vessel 310 and illumination control for the imaging unit 120. The vessel edge detection processing will be explained with reference to the flowchart show in FIG. 8.

In step S301, the first control section 110 obtains information relating to in which direction of the X direction and the Y direction the imaging unit 120 is currently moved by the driving mechanism 160. If this step is performed for the first time in the repeated processing, the direction of the current movement of the imaging unit 120 obtained by the first control section 110 is, for example, the X direction. Subsequently, the vessel edge detection processing advances to step S302.

Figure 9:
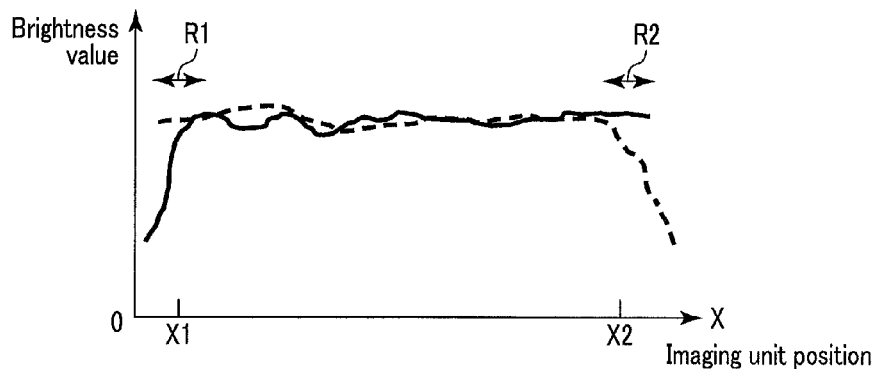
FIG. 9 is a view for explaining vessel edge detection at a time of image acquisition by the imaging unit according to the first embodiment.

In step S302, the first control section 110 determines whether the edge portion of the vessel 310 is detected in the direction of the current movement of the imaging unit 120 recognized in step S301. Detection of the vessel edge portion has been described with reference to FIGS. 5A-5C; however, it will be described in more detail with reference to FIG. 9. FIG. 9 shows the relationship between a brightness value included in an image signal acquired by the imaging section 170 and a position of the imaging unit 120 in a case in which an aperture value (AV), and a shutter speed (time value, TV) are fixed. In this case, brightness information included in the image signal or a change in brightness value detected from the image signal follows a change in brightness of an object to be imaged. Therefore, in this case, the brightness value changes depending on the amount of flux of light, that is, the amount of light, received by the imaging section 170. The relationship between a brightness value and a position of the imaging unit 120 shown in FIG. 9 illustrates an example of illumination control performed when the imaging unit 120 is moved in the X direction, and relates to control of switching between the first illumination section 180a and the second illumination section 180b. The ends in the X direction of the vessel 310, that is, the positions of the vessel edge, are denoted by X1 and X2. In FIG. 9, the broken line represents a case in which the first control section 110 causes the second illumination section 180b to light and the imaging unit 120 to move in the X+ direction. The solid line represents a case in which the first control section 110 causes the first illumination section 180a to light and the imaging unit 120 to move in the X− direction. In general, a distribution of the cells 324 in the vessel 310 is almost constant; therefore, the amount of change in brightness (transmittance) in accordance with a position in a range of imaging is relatively small. Accordingly, the amount of change in brightness in accordance with a position of the cell 324 is sufficiently smaller than the amount of change in brightness due to scattering of illumination light at the edge portions of the vessel 310.

As described above, when illumination light scatters in the edge portions of the vessel 310, the amount of light received by the imaging section 170 and the brightness value are reduced. First, a case in which the imaging unit 120 moves from one end in the X− direction of the vessel 310 (position X1) toward the X+ direction will be explained. In this case, the second emitting section 183b emits illumination light. The initial position of the imaging unit 120 at this time is a position at which illumination light emitted from the second emitting section 183b can be incident on the vessel top plate 360 of the vessel 310 and the imaging section 170 can receive the reflected light.

At this time, as indicated by the broken line in FIG. 9, when the imaging unit 120 moves from X1 to a certain distance in the X+ direction, the brightness value detected by the imaging section 170 does not significantly change and illumination suitable for imaging is maintained. When the imaging unit 120 further moves in the X+ direction and reaches the end in the X+ direction of the vessel 310 (position X2), the amount of illumination light that is emitted from the second emitting section 183*b* and is scattered in the edge portion of the vessel 310 drastically increases. Specifically, as indicated by the broken line in FIG. 9, in an exposure change region R2, the amount of reflected light that can be acquired by the imaging section 170 drastically reduces and the brightness value also drastically decreases.

The first control section 110 detects the vessel edge portion based on detection of the exposure change region R2. The same applies to a case in which the first emitting section 183*a* emits illumination light and the imaging unit 120 moves from one end in the X+ direction of the vessel 310 toward another end in the X− direction. In this case, the brightness value changes as indicated by the solid line in FIG. 9. The first control section 110 detects the vessel edge portion based on detection of the exposure change region R1. As described above, when imaging is performed with the imaging unit 120 being moved, the first control section 110 causes the emitting section that is located in the direction of the forward movement side to emit illumination light, and switches between the emitting sections when an image signal, for example, a brightness value included in the image signal changes. If the first control section 110 detects an edge of the vessel 310, that is, a vessel edge portion, the vessel edge detection processing advances to step S303. If not, the vessel edge detection processing is ended and proceeds to step S205 of the scan processing. Furthermore, the first control section 110 acquires position information of the imaging unit 120 upon detection of the vessel edge portion, and records it in the first storage section 130 or the second storage section 230. Besides the edge portion of the vessel 310, an object to be observed, such as a cell, may also cause scattering of illumination light. Scattering of illumination light in the vessel edge portion and scattering in an object to be observed, such as a cell, are distinguishable, because they are different in intensity or degree.

In step S303, the first control section 110 switches illumination. In this embodiment, if, at that time, the illumination light is emitted from the first emitting section 183*a*, the first control section 110 switches the emitting section that emits illumination light (lighting emitting section) to the second emitting section 183*b*. If the illumination light is emitted from the second emitting section 183*b* at that time, the first control section 110 switches the emitting section that emits illumination light (lighting emitting section) to the first emitting section 183*a*. After switching the illumination, the vessel edge detection processing advances to step S304.

In step S304, the first control section 110 images the sample 300 at the current position. The imaging performed by the first control section 110 is similar to that in step S203 described above. After the imaging, the vessel edge detection processing advances to step S305.

In step S305, the first control section 110 determines whether or not the image acquired in step S304 is proper. If the acquired image is proper, it follows that, for example, the imaging optical system 172 could sufficiently receive reflected light, that is, the illumination light reflected by the vessel top plate 360 of the illumination light emitted from the illumination optical system 182. The first control section 110 computes a brightness value from the image data, and determines whether or not the computed brightness value is greater than a predetermined value. An average brightness value of all pixels of acquired image data may be adopted as the computed brightness value. Alternatively, an average brightness value in a partial area that is a part of the image or a peak value or bottom value of the brightness values of the partial area may be adopted. If the acquired image is determined to be proper, the vessel edge detection processing advances to step S306. If not, the vessel edge detection processing advances to step S307.

In step S306, since the image acquired in step S304 is proper, the first control section 110 replaces the image acquired in step S203 with the image acquired in step S304. In other words, the first control section 110 selects the image acquired in this step as an image to be recorded. At this time, the first control section 110 does not switch the illumination. In this step, since the result of imaging after switching the illumination is proper, the first control section 110 determines that the position information relating to the vessel edge portion recorded in step S302 actually represents the vessel edge portion. Subsequently, the vessel edge detection processing is ended and proceeds to step S205 of the scan processing.

In step S307, the first control section 110 returns the illumination to that used before switching in step S303, and the image acquired in step S304 is discarded. In other words, the image acquired in step 203 is recorded as an image to be recorded. Since results of imaging before and after switching the illumination are both improper, the first control section 110 removes position information relating to the current position from all position information relating to the vessel edge portion recorded in step S302. Subsequently, the vessel edge detection processing advances to step S308.

In step S308, the first control section 110 registers the current position of the imaging unit 120, the information on the lit illumination optical system, etc. as error information. Subsequently, the vessel edge detection processing is ended and proceeds to step S205 of the scan processing. After the error information is registered, the processing may return to step S203, in which imaging may be performed again. In step S302 to step S305 and step S307, the illumination light may be determined to be scattered not by the edge portion of the vessel 310 but by an object to be observed, such as the cell 324. The first control section 110 may record the position information at the position where the cell 324 or the like is present as an edge portion of an area for which data should be intensively collected. If the illumination light is scattered by the object to be observed, such as the cell 324, a proper image may also not be acquired in a part near the object. Therefore, presence or absence of the cell 324 or the like may be determined based on position information and an image at or near the imaging position for which error information is recorded.

Furthermore, if the amount of movement of one time of the imaging unit 120 is not appropriate, a proper image may not be acquired in both before and after switching the illumination. In this case, the first control section 110 may reset the amount of movement. Alternatively, after reversing the setting of the direction of movement of the imaging unit 120 as will be described later in the explanation of subsequent steps, the movement may be continued until the edge portion of the vessel 310 is detected. As described above, the first control section 110 detects the vessel edge portion and performs illumination control based on a change of brightness information included in an image or image signal newly acquired by imaging from brightness information included in an image or image signal previously acquired, that is, a change in brightness information included in an image signal or temporal change.

In step S205, the first control section 110 determines whether or not a scan in the X direction should be ended. If the first control section 110 determines that there is an edge portion of the vessel 310 in the position of the imaging unit 120, for example, if the first control section 110 determines that a proper image is acquired in step S304 in the vessel edge detection processing, it determines that the scan in the X direction should be ended. The case of determination to be ended includes a case in which the position of the vessel edge portion is known and the current position is determined to be the vessel edge portion based on the known position information, for example, a case in which the scan processing has been previously performed. If it is determined that the scan in the X direction should be ended, the scan processing advances to step S207, and if not, the scan processing advances to step S206.

In step S206, the first control section 110 causes the driving mechanism 160 to move the imaging unit 120 in the X direction by a predetermined amount. Subsequently, the scan processing returns to step S203.

In step S207, the first control section 110 determines whether or not the scan processing is to be ended. The first control section 110 determines that the scan processing is to be ended, if, for example, scan of a predetermined range is ended. The predetermined range is, for example, a range based on presetting. If the scan processing is to be ended, it advances to step S108 in the observation apparatus control processing, and if not, the scan processing advances to step S208.

In step S208, the first control section 110 causes the driving mechanism 160 to move the imaging unit 120 in the Y direction by a predetermined amount. The first control section 110 reverses the setting of the direction of movement in the X direction. Specifically, for example, in the movement of the imaging unit 120 immediately before this step, if the direction of movement is the X+ direction, the first control section 110 switches the direction of movement to the X− direction. Subsequently, the scan processing returns to step S203.

For example, in the process of repeating steps S203 to S206 immediately after the first control section 110 causes the imaging unit 120 to move in the Y direction by the predetermined amount, if the vessel edge portion is continuously detected predetermined times both in the X and Y directions, the first control section 110 determines that the current position is at the vessel edge portion both in the X and Y directions. Though not limited to the above case, if the first control section 110 determines that the current position is at the vessel edge portion both in the X and Y directions, it can determine that the scan processing should be completed at that position. Since the initial position of scan is assumed to be the center of the vessel 310, only the area in the Y+ direction from the initial position has been scanned so far. Therefore, to scan also the Y− direction from the initial position, after moving the imaging unit 120 to the initial position of the scan processing, the first control section 110 may reverse the setting of the direction of movement in the Y direction, and may execute the scan processing described above until the imaging unit 120 reaches the vessel edge portion of the opposite end. Furthermore, the entire region of the sample 300 may be scanned by setting the amount of movement in the Y direction to move the imaging unit 120 alternately in the Y+ direction and the Y− direction.

Referring back to FIG. 6, the observation apparatus control processing after the completion of the scan processing will be described. After the scan processing, the observation apparatus control processing advances to step S108. In step S108, the first control section 110 determines whether or not manual position designation is performed. To be specific, it is determined whether an imaging instruction is received from the controller 200 with designation of an imaging position. For example, the user can designate a position based on the image of the entire sample 300 obtained by the scan processing, information on a position for which error information is recorded, etc. The user can also designate an imaging position based on an image previously obtained by imaging in connection with measurement, instead of the images obtained by the scan processing. Unless an imaging instruction designating an imaging position is received, the observation apparatus control processing advances to step S110. If an imaging instruction is received, the observation apparatus control processing advances to step S109.

In step S109, the first control section 110 causes the driving mechanism 160 to move the imaging section 170 to a designated position and causes the imaging section 170 to acquire an image at that position. The first control section 110 transfers the acquired image to the controller 200 by way of the first communication device 192. Subsequently, the observation apparatus control processing advances to step S110.

In step S110, the first control section 110 determines whether or not the current time is a time when the measurement should be started. Unless the current time is a measurement start time, the processing advances to step S112. If the current time is a measurement start time, the processing advances to step S111. The measurement start time may be predetermined, for example, at the intervals of one hour. The measurement start condition need not depend on time, but may depend on the state of the cell 324 or medium 322. In the present embodiment, measurement is repeatedly performed whenever the measurement start time comes.

In step S111, the first control section 110 performs measurement processing. In other words, the first control section 110 causes the imaging section 170 to repeatedly perform imaging, while simultaneously causing the driving mechanism 160 to move the imaging section 170. The first control section 110 performs predetermined processing for an obtained image and records a requested result in the first storage section 130. Subsequently, the processing advances to step S112.

A range of movement of the imaging section 170 by the driving mechanism 160 in the measurement processing is determined based on, for example, position information of the edge portion of the vessel 310 acquired by the first control section 110 through the scan processing and stored in the first storage section 130 or the second storage section 230. The range of movement may be set by the user.

The range imaged by the measurement processing is, for example, the following range. For example, the range imaged by the measurement processing is a range in which the sample 300 is specified as being arranged, based on the position information of the edge portion of the vessel 310 obtained by the scan processing. Alternatively, the range imaged by the measurement processing is a range in which cells of interest, such as a cell colony, are specified as being located, at the start of measurement. Alternatively, the range imaged by the measurement processing is a range in which the occurrence of a noteworthy change in a cell or the like is indicated by the imaging performed a number of times. Whether there are cells of interest, such as a cell colony, and whether there is a range in which a noteworthy change occurs in a cell or the like may be determined based on information on a position at which illumination light is scattered other than the position that is determined to be an edge portion of the vessel 310 in the scan processing.

In the above description, a still image is taken in the scan processing, but this is not restrictive. Both in the scan processing and the measurement processing, still images may be taken for the respective position coordinates of the imaging section 170, and analysis may be performed based on the still images. Instead, moving images may be captured.

As described above, according to the technique of this embodiment, a position of the vessel edge portion is acquired based on a change in brightness value, and illumination control is performed based on detection of a vessel edge portion or the acquired position information of the vessel edge portion. Specifically, the first control section 110 detects a position of the vessel edge portion based on an image signal. Based on information of the detected position of the vessel edge portion, the first control section 110 determines which of the emitting sections of the illumination section that emit the illumination light should emit illumination light, and if necessary, switches between the emitting sections that emit the illumination light. Furthermore, detection of a position of the vessel edge portion based on an image signal is based on a change, in particular a decline, of a brightness value included in the image signal.

Due to the illumination control, even when the position of the vessel edge portion is unknown or when a part near the vessel edge portion is imaged, imaging and measurement can be performed in appropriate environments of illumination without excess or deficiency. Therefore, by utilizing the technique of this embodiment, the measurement system 1 and the observation apparatus 100 can operate and produce a satisfactory image while saving energy.

Figure 4:
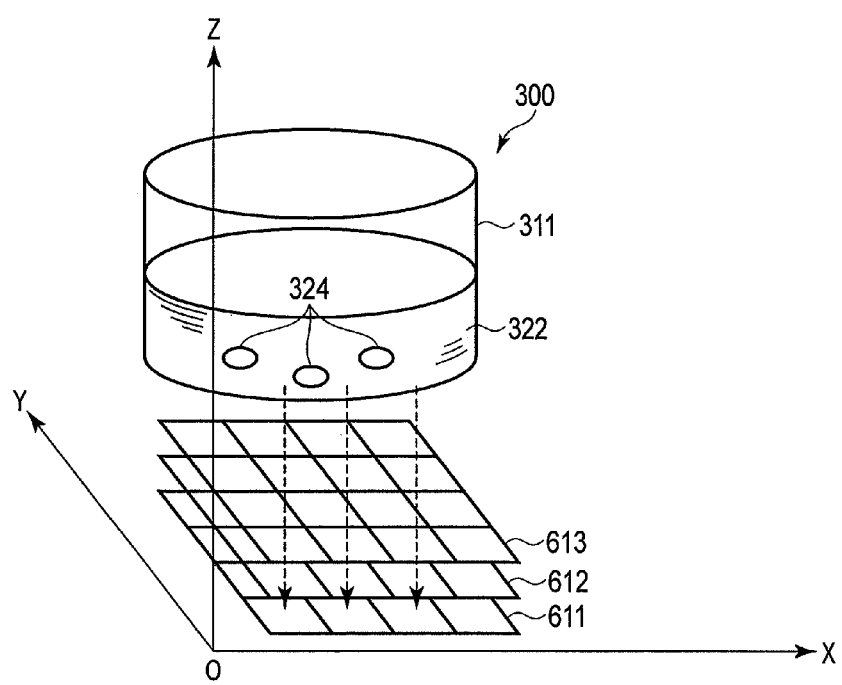
FIG. 4 is a view for explaining image acquisition by an observation apparatus according to the first embodiment.
Figure 10:
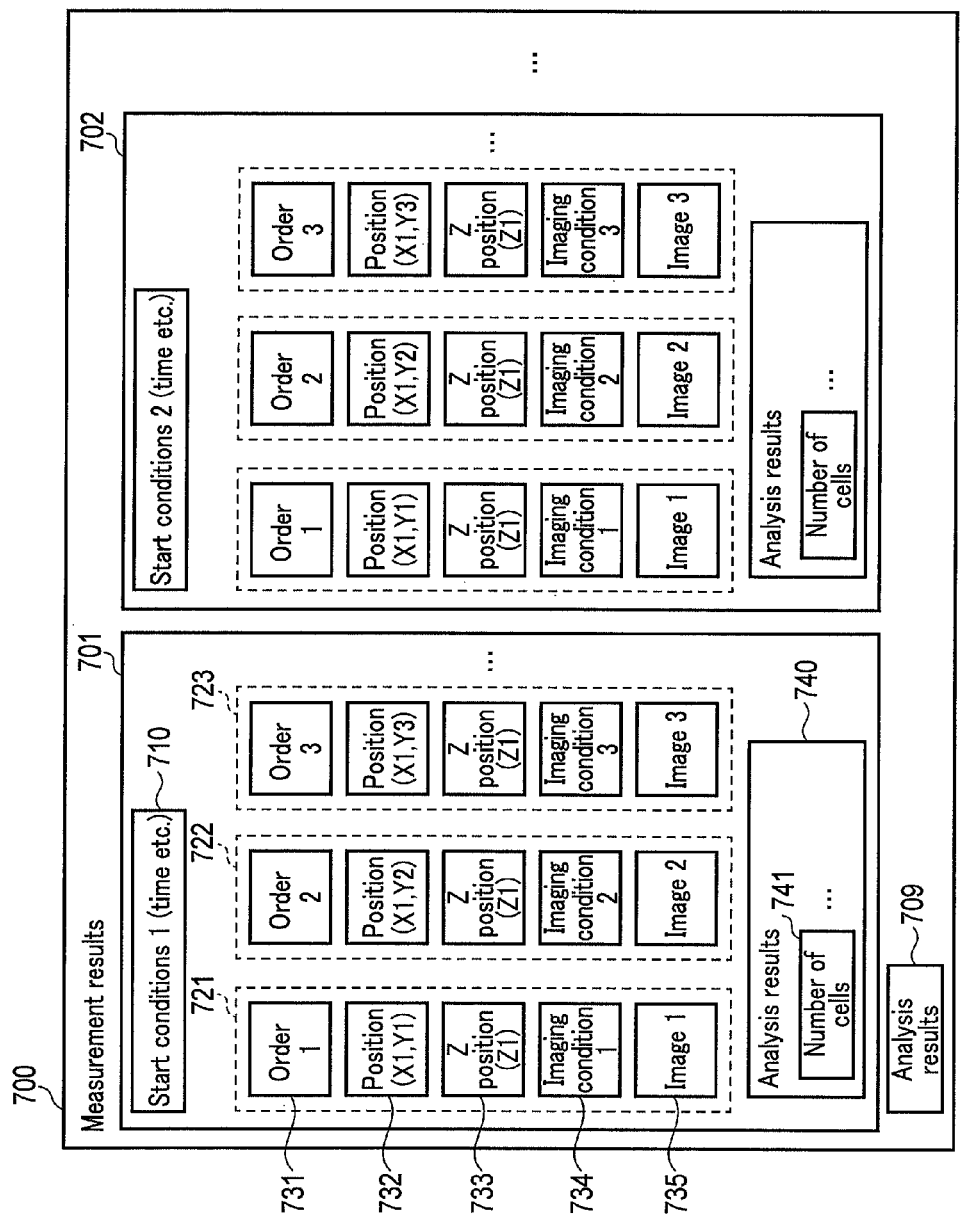
FIG. 10 is a diagram showing an outline of a configuration example of data of measurement results obtained by the measurement system according to the first embodiment.

Image acquisition performed in the measurement processing has been described with reference to FIG. 4. An example of a data structure of measurement results obtained as above and stored in the first storage section 130 is shown in FIG. 10. As shown in FIG. 10, measurement results 700 include first data 701 obtained by a first-time measurement, second data 702 obtained by a second-time measurement, etc. The number of data items increases or decreases in accordance with the number of times measurement is performed.

The first data 701 will be described by way of example. The first data 701 includes a start condition 710. This start condition 710 includes a condition under which the measurement start is determined in step S110. For example, a measurement start time is predetermined, and when measurement is started at this measurement start time, the measurement start time is recorded as the start condition 710.

In the first data 701, first image information 721, second image information 722, third image information 723, etc. are recorded. Each of these data is a set of data acquired in one-time imaging. The first image information 721 will be described by way of example. The first image information 721 includes an order 731, a position 732, a Z position 733, an imaging condition 734, and an image 735. The order 731 is indicated by serial numbers which are assigned to the imaging operations performed for respective positions. The position 732 includes an X coordinate and a Y coordinate of an imaging position. The X coordinate and the Y coordinate are values used in the control of the driving mechanism 160 and may be acquired by the position control section 111, for example. The Z position 733 includes a Z coordinate of an imaging position. The Z coordinate is a value used in the control of the imaging optical system 172 and may be acquired by the imaging control section 112, for example. The imaging condition 734 includes exposure conditions, such as a shutter speed and an aperture value, and other imaging conditions. The imaging conditions may differ, depending upon each imaging operation, they may be the same for the imaging operations included in the first data 701, or they may be the same for all imaging operations included in the measurement results 700. The image 735 is image data obtained by the imaging. Likewise, each of the second image information 722 and the third image information 723 includes information regarding an order, a position, a Z position, an imaging condition and an image. Where an imaging plane is not moved in the Z direction, the information on the Z position may be omitted.

The first data 701 includes analysis results 740. The analysis results 740 include a cell number 741 representing the number of cells or cell groups measured by the image processing circuit 140. The analysis results 740 may also include a plane image obtained by synthesizing the images of the same Z position. The analysis results 740 may also include a three-dimensional image obtained by synthesizing all images 735. The analysis results 740 may include a depth-synthesis image.

Like the first data 701, the second data 702 may include a start condition, first image data, second image data, third image data, analysis results, etc.

The measurement results 700 can include analysis results 709 of all measurements that are obtained based on the first data, second data, etc. All measurement results 700 may be recorded in one file; alternatively, part of the measurement results 700 may be recorded in one file.

Returning to FIG. 6, the description will be continued. In step S112, the first control section 110 determines whether or not a request for information is made by the controller 200. For example, the data obtained in step S111 is requested by the controller 200. Unless the request for information is made, the processing advances to step S114. If the request for information is made, the processing advances to step S113.

In step S113, the first control section 110 transfers the information requested by the controller 200 to the controller 200 through the first communication device 192. Subsequently, the processing advances to step S114.

In step S114, the first control section 110 determines whether or not the observation apparatus control processing should be ended. If it is determined that the observation apparatus control processing should be ended, the observation apparatus control processing is brought to an end. For example, when a series of measurements are ended and the observation apparatus 100 is removed from the incubator, the observation apparatus control processing is brought to an end. Unless the observation apparatus control processing is brought to an end, the processing advances to step S115.

In step S115, the first control section 110 determines whether or not the power source should be turned off. For example, if the standby time, which is from the measurement in step S111 to the next measurement, is long, the first control section 110 determines that the power source should be turned off to suppress the power consumption. Unless the power source is turned off, the processing returns to step S104. If it is determined that the power source should be turned off, the processing advances to step S116.

In step S116, the first control section 110 turns off each portion of the observation apparatus 100. Subsequently, the processing returns to step S101. In the above manner, the observation apparatus 100 repeatedly performs measurement.

Next, the operation of the controller 200 will be described with reference to the flowcharts shown in FIGS. 11A and 11B. The processing indicated in the flowcharts of FIGS. 11A and 11B starts when the observation apparatus 100, the controller 200 and the sample 300 are set in place.

In step S401, the second control section 210 determines whether or not a measurement program according to the present embodiment is activated. Unless the measurement program is activated, the processing of step S401 is repeated. The controller 200 is not limited to the functions of the controller of the measurement system of the present embodiment but may have various functions. Therefore, when the measurement program is not activated, the controller 200 may operate as a system other than the measurement system 1. If it is determined that the measurement program is activated, the processing advances to step S402.

In step S402, the second control section 210 establishes communications with the observation apparatus 100. This operation is related to step S103 of the observation apparatus control performed by the observation apparatus 100; that is, the observation apparatus 100 and the controller 200 operate so that communications between them are established. Subsequently, the processing performed by the controller advances to step S403. The communications established then may be low-power-consumption communications that is irrelevant to step S103 of the observation apparatus control processing and that only enables the transfer of an instruction to turn on the observation apparatus 100.

In step S403, the second control section 210 determines whether or not the user is requesting that the observation apparatus 100 be turned on. For example, if an instruction to turn on the observation apparatus 100 is supplied from the input device 274, the second control section 210 determines that the user is requesting that the power source be turned on. Unless the instruction to turn on the observation apparatus 100 is supplied, the processing advances to step S405. If the instruction to turn on the observation apparatus 100 is supplied, the processing advances to step S404. In step S404, the second control section 210 transfers an instruction to turn on the observation apparatus 100 to the observation apparatus 100. Subsequently, the processing advances to step S405. This operation is related to step S101 of the observation apparatus control processing performed by the observation apparatus 100. Upon receipt of the instruction to turn on the observation apparatus 100 from the controller 200, the observation apparatus 100 is turned on in step S102. The communication means used in the embodiment may be low-power-consumption communications such as Bluetooth Low Energy.

In step S405, the second control section 210 determines whether or not the user is requesting transfer of information to the observation apparatus 100. For example, if an instruction to transfer information is supplied from the input device 274, the second control section 210 determines that the user is requesting transfer of information. The information the transfer of which is requested is information on measurement conditions etc. Unless the transfer of information is requested, the processing advances to step S407. If the transfer of information is requested, the processing advances to step S406. In step S406, the second control section 210 transfers the information entered from the input device 274 to the observation apparatus 100. Subsequently, the processing advances to step S407. This operation is related to step S104 of the observation apparatus control processing performed by the observation apparatus 100. The observation apparatus 100 acquires the information transferred from the controller 200 to the observation apparatus 100 in step S105.

In step S407, the second control section 210 determines whether or not the user is requesting that the observation apparatus 100 perform scan processing. For example, if an instruction related to execution of the scan processing is supplied from the input device 274, the second control section 210 determines that the user is requesting execution of the scan processing. Unless the scan processing is requested, the processing advances to step S409. If the scan processing is requested, the processing advances to step S408. In step S408, the second control section 210 transfers an instruction to start the scan processing to the observation apparatus 100. Subsequently, the processing advances to step S409. This operation is related to step S106 of the observation apparatus control processing performed by the observation apparatus 100. The observation apparatus 100 performs scan processing in step S107, based on the scan processing start instruction transferred from the controller 200 to the observation apparatus 100.

In step S409, the second control section 210 determines whether or not the user manually designates a position to be imaged by the observation apparatus 100. For example, if an imaging position is entered from the input device 274, the second control section 210 determines that imaging position has been designated. Unless the imaging position is designated, the processing advances to step S411. If the imaging position is designated, the processing advances to step S410. In step S410, the second control section 210 transfers the imaging position entered from the input device 274 to the observation apparatus 100. Subsequently, the processing advances to step S411. This operation is related to step S108 of the observation apparatus control processing performed by the observation apparatus 100. Position adjustment is made in step S109 in accordance with the imaging position transferred from the controller 200 to the observation apparatus 100. An image is acquired at that position and transferred to the controller 200 in step 109.

In step S411, the second control section 210 determines whether or not the user is requesting that the observation apparatus 100 start measurement. For example, if an instruction to start measurement by the observation apparatus 100 is supplied from the input device 274, the second control section 210 determines that the user is requesting the start of measurement. If the start of measurement is not requested, the processing advances to step S413. If the start of measurement is requested, the processing advances to step S412. In step S412, the second control section 210 transfers an instruction to start measurement to the observation apparatus 100. Subsequently, the processing advances to step S413. This operation is related to step S110 of the observation apparatus control processing performed by the observation apparatus 100. Measurement is performed in step S111 in accordance with the instruction transferred from the controller 200 to the observation apparatus 100.

In step S413, the second control section 210 determines whether or not the user is requesting acquiring information from the observation apparatus 100. For example, if an instruction to request information is supplied from the input device 274, the second control section 210 determines that the user is requesting information. The information requested then is, for example, information on the sample 300 obtained by the observation apparatus 100. The information can be information contained in the measurement results 700 described with reference to FIG. 9, including image data on the sample 300 and the number of cells or cell groups in the sample 300. Unless the information is requested, the processing advances to step S415. If the information is requested, the processing advances to step S414. In step S414, the second control section 210 transfers an instruction to transfer the user's requested information to the observation apparatus 100. Subsequently, the processing advances to step S415. This operation is related to step S112 of the observation apparatus control processing performed by the observation apparatus 100. The information requested in step S113 is transferred from the observation apparatus 100 to the controller 200 in accordance with the information request transferred from the controller 200 to the observation apparatus 100.

In step S415, the second control section 210 determines whether or not the information requested in step S414 is received. Unless the information is received, the processing advances to step S417. If the information is received, the processing advances to step S416. In step S416, the second control section 210 causes the received information to be displayed on the display 272 or to be recorded in the second storage section 230. Subsequently, the processing advances to step S417.

In step S417, the second control section 210 determines whether or not the user is requesting that the observation apparatus 100 be turned off. For example, if an instruction to turn off the observation apparatus 100 is supplied from the input device 274, the second control section 210 determines that the user is requesting that the power source be turned off. Unless the instruction to turn off the observation apparatus 100 is supplied, the processing advances to step S419. If the instruction to turn off the observation apparatus 100 is supplied, the processing advances to step S418. In step S418, the second control section 210 transfers an instruction to turn off the observation apparatus 100 to the observation apparatus 100. Subsequently, the processing advances to step S419. This operation is related to step S115 of the observation apparatus control processing performed by the observation apparatus 100. The observation apparatus 100 is turned off in step S116 in accordance with the turn-off instruction transferred from the controller 200 to the observation apparatus 100.

In step S419, the second control section 210 determines whether or not the measurement program comes to an end. If the measurement program ends, the processing returns to step S401. Unless the measurement program ends, the processing returns to step S403. As can be seen from this, the above operation is repeatedly executed.

As described above, the measurement by the measurement system 1 can be repeatedly performed at predetermined timings and under predetermined conditions. Measurement timings and measurement conditions may be entered by the user from the controller 200 and set in the observation apparatus 100. The measurement by the measurement system 1 may be manually performed based on a user's instruction when the instruction to start the measurement is entered by the user from the controller 200 and is supplied to the observation apparatus 100.

Advantage of the Measurement System

The measurement system 1 of the present embodiment can obtain an image of cells existing in a wide range in the state where the sample 300 is statically placed in the incubator. It should be noted that an image can be repeatedly obtained with time. The user can therefore observe how the cells change with time and analyze the change. According to the present embodiment, scan processing is performed. In the scan processing, the first control section 110 performs controlling to determine which of the emitting sections should emit illumination light based on an image signal acquired by the imaging unit 120. In other words, through the scan processing, the user can acquire an image and measurement data under appropriate illumination control even in a part near the edge portion of the vessel for the sample 300. In addition, based on the images obtained in the scan processing, information on an area for which data should be intensively collected in the subsequent measurement can be acquired. Furthermore, according to the technique of the embodiment, a position of an object to be observed, such as cells 324, can also be acquired based on a change in brightness value. Therefore, the aforementioned information on an area for which data should be intensively collected includes information on generation, disappearance, deformation, etc. of the cells in the area. Thus, the technique of the embodiment detects a vessel edge portion based on a change in an image signal, for example, a decline in brightness value, with movement of the imaging unit 120. In addition, according to the technique of the embodiment, based on information of the detected position of the vessel edge portion, an emitting section that emits illumination light is determined, and if necessary, switched. Thus, the measurement system 1 and the observation apparatus 100 of the embodiment can operate in appropriate environments of illumination without excess or deficiency and can produce a satisfactory image while saving energy.

Second Embodiment

A second embodiment of the present invention is explained below. In the following, matters different from the first embodiment will be explained. Identical symbols will be used for identical parts, and detailed explanations thereof will be omitted. In the first embodiment, the first control section 110 switches between the emitting sections of the two illumination optical systems to emit illumination light. In contrast, in the second embodiment, an imaging unit 120 shown in FIG. 12 further comprises a third emitting section 183c and a fourth emitting section 183d. The first control section 110 switches between the four emitting sections to emit illumination light. The imaging unit 120 may further comprise a third illumination optical system and a fourth illumination optical system, and the light source 184 may further comprise a third light source and a fourth light source. As well as the first embodiment described above, each of the emitting sections may be included in either of the third illumination system or the third light source, or either of the fourth illumination system or the fourth light source. The first control section 110 moves the imaging unit 120 by the driving mechanism 160 in not only the X direction but also the Y direction.

Referring to FIG. 12, an example of the configuration of the imaging unit 120 of this embodiment will be explained in detail. The emitting sections are arranged almost symmetrically with respect to the imaging section 170 or the imaging optical system 172. The imaging section 170 or the imaging optical system 172 is arranged between the emitting sections. Specifically, the third emitting section 183c and the fourth emitting section 183d are arranged almost symmetrically with respect to the imaging optical system 172. A line segment connecting the position of the third emitting section 183c and the position of the fourth emitting section 183d is almost perpendicular to a line segment connecting the position of the first emitting section 183a and the position of the second emitting section 183b. For example, the first emitting section 183a is provided on a side of the X− direction of the imaging optical system 172, the second emitting section 183b is provided on a side of the Y− direction of the imaging optical system 172, the third emitting section 183c is provided on a side of the X+ direction of the imaging optical system 172, and the fourth emitting section 183d is provided on a side of the Y+ direction of the imaging optical system 172. The configuration of the imaging unit 120 described above is not limited to the example described above. Arrangement of the elements of the imaging unit 120 in the X-axis direction and the Y-axis direction is not limited to the example described above. For example, the second emitting section 183b and the fourth emitting section 183d may be positioned in the X-axis direction. Alternatively, an arrangement in which the configuration shown in FIG. 12 is rotated on the same plane may be employed.

Figure 13:
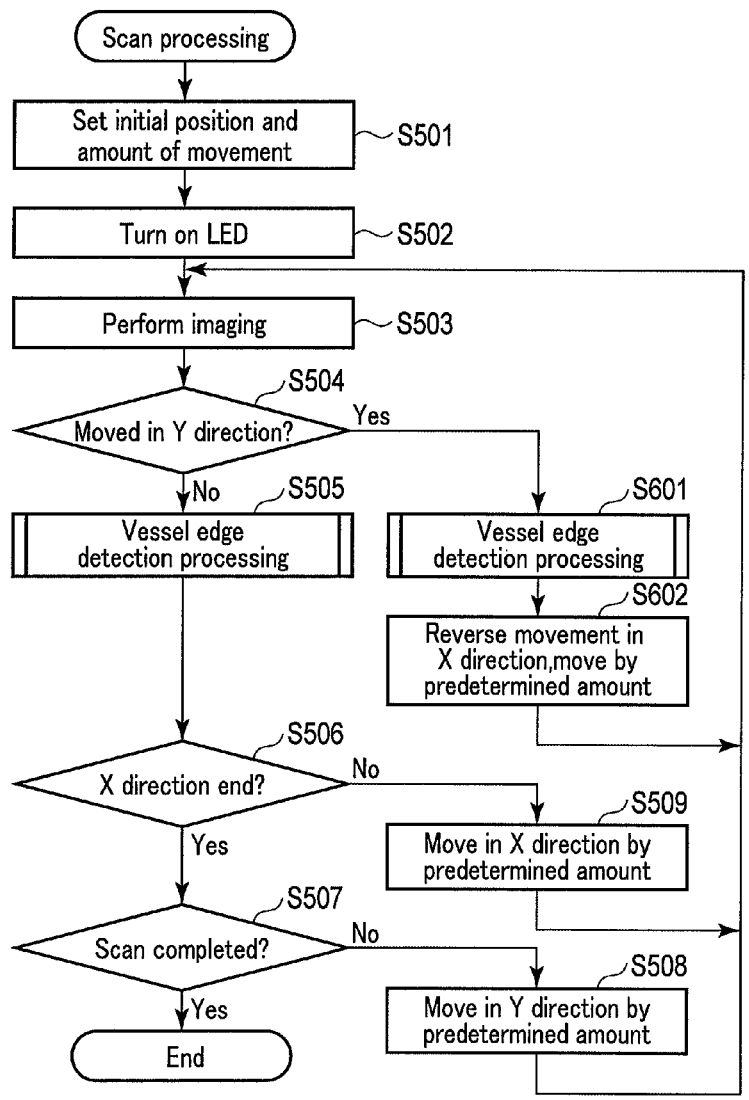
FIG. 13 is a flowchart illustrating an example of scan processing according to the second embodiment.

The scan processing of this embodiment will be described with reference to the flowchart shown in FIG. 13. The scan processing in this embodiment corresponds to the scan processing in the first embodiment plus the vessel edge detection processing and the illumination control in the Y direction.

Figure 7:
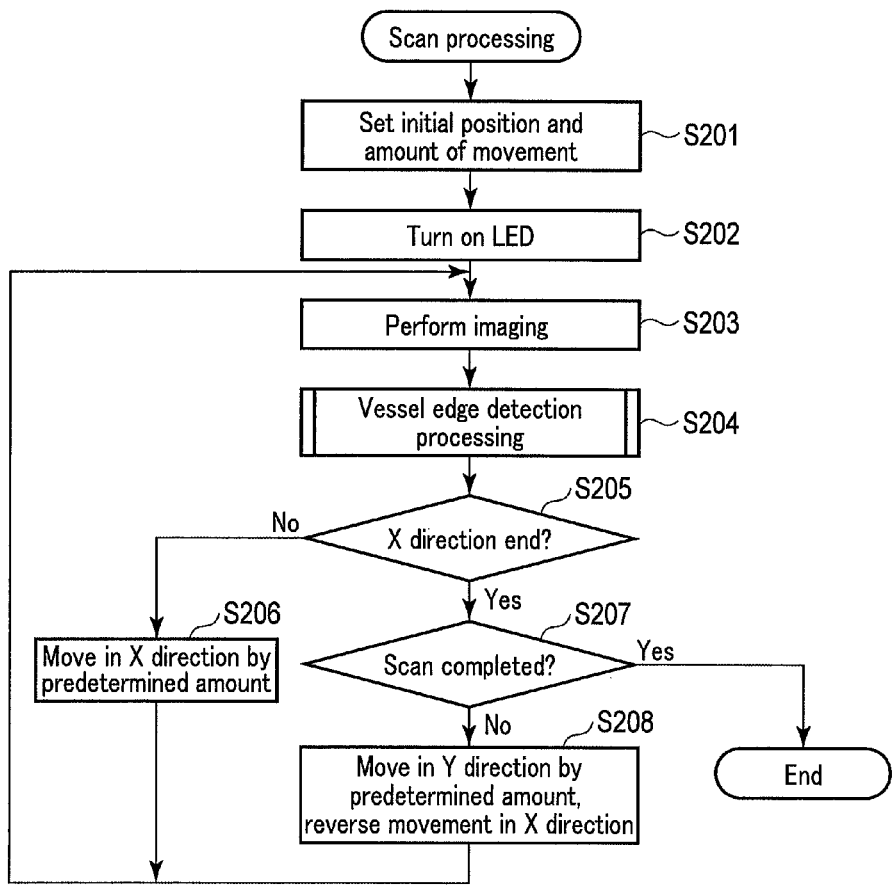
FIG. 7 is a flowchart illustrating an example of scan processing according to the first embodiment.

In step S501, the first control section 110 sets the initial position and the amount of movement of the imaging unit 120 in the same manner as in step S201 of the scan processing shown in FIG. 7. Subsequently, the processing advances to step S502. In step S502, the first control section 110 may turn on illumination in accordance with the direction of the first movement in the same manner as in step S202 of the scan processing shown in FIG. 7. For example, when the direction of the first movement is set to the X+ direction, the second illumination optical system 182b located in the direction of the forward movement of the imaging unit 120 is selected as the emitting section that emits illumination light. At that time, the emitting section that emits illumination light may further include one or both of the third illumination optical system and the fourth illumination optical system. The third illumination optical system or the fourth illumination optical system may be selectively lit in accordance with the setting of the direction of movement; for example, if the direction of the first movement in the Y direction is the Y+ direction, the fourth illumination optical system may be selected. Subsequently, the processing advances to step S503. In step S503, the first control section 110 performs imaging in the same manner as in step S203 of the scan processing shown in FIG. 7. Subsequently, the processing advances to step S504. In step S502, if the direction of the first movement is the X+ direction, the first illumination optical system 182a located in the direction opposite to the forward movement of the imaging unit 120 may be selected as the emitting section that emits illumination light.

In step S504, the first control section 110 determines whether or not the imaging unit 120 was moved in the Y direction before the imaging in the step S503, that is, in the last repeated processing in step S508 to be described later. If the imaging in step S503 is determined to be performed after the imaging unit 120 was moved in the Y direction, the scan processing advances to step S601. If the imaging is determined to not be performed after the imaging unit 120 was moved in the Y direction, the scan processing advances to step S505.

Figure 8:
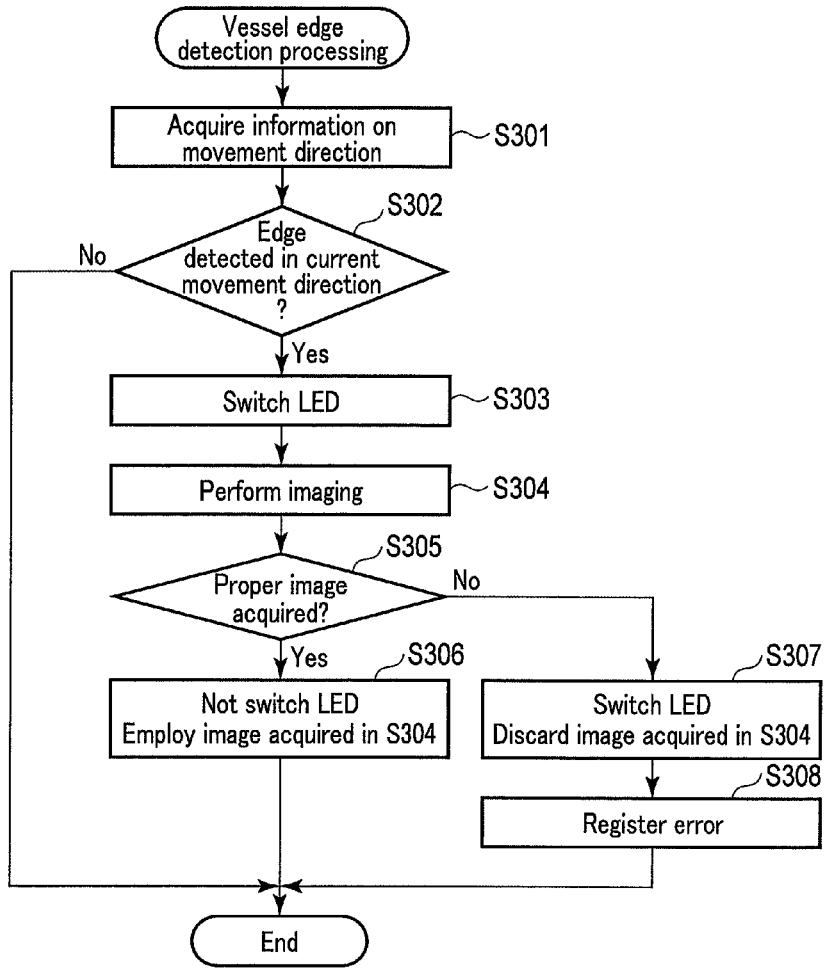
FIG. 8 is a flowchart illustrating an example of vessel edge detection processing according to the first embodiment.

In step S505, the first control section 110 performs the vessel edge detection processing shown in FIG. 8. In step S301 of the vessel edge detection processing, the direction of movement at this time is the X direction, and it is determined whether or not an edge portion of the vessel 310 is detected in the X direction. The first control section 110 moves the imaging unit 120 and repeats imaging, while performing illumination control, such as switching of LEDs, in accordance with detection of the vessel edge portion. After the vessel edge detection processing is ended, the scan processing advances to step S506.

In step S506, the first control section 110 determines whether or not a scan in the X direction should be ended, in the same manner as in step S205 of the scan processing shown in FIG. 7. If it is determined that the scan in the X direction should be ended, the scan processing advances to step S507, and if not, the scan processing advances to step S509. In step S507, the first control section 110 determines whether or not the scan processing should be ended in the same manner as in step S207 of the scan processing shown in FIG. 7. If it is determined that the scan processing should be ended, the processing advances to step S108 in the observation apparatus control processing, and if not, the scan processing advances to step S508.

In step S508, the first control section 110 moves the imaging unit 120 in the Y direction by a predetermined amount in the same manner as in step S208 of the scan processing shown in FIG. 7. After the movement in the Y direction, unlike step S208, the setting of the direction of movement in the X direction is not reversed. Subsequently, the scan processing returns to step S503.

In step S509, the first control section 110 causes the driving mechanism 160 to move the imaging unit 120 in the X direction by a predetermined amount in the same manner as in step S206 of the scan processing shown in FIG. 7. Subsequently, the scan processing returns to step S503.

In step S601, the first control section 110 performs the vessel edge detection processing shown in FIG. 8. In step S301 of the vessel edge detection processing, the direction of movement at this time is the Y direction, and it is determined whether or not an edge portion of the vessel 310 is detected in the Y direction. The first control section 110 moves the imaging unit 120 and repeats imaging, while performing illumination control, such as switching of LEDs, in accordance with detection of the vessel edge portion. After the vessel edge detection processing is ended, the scan processing advances to step S602.

In step S602, the first control section 110 reverses the setting of the direction of movement in the X direction. After reversing the setting of the direction of movement in the X direction, the first control section 110 causes the driving mechanism 160 to move the imaging unit 120 in the X direction by a predetermined amount. Subsequently, the scan processing returns to step S503. As described above, in this embodiment, the first control section 110 causes the driving mechanism 160 to move the imaging unit 120 in the X and Y directions, and when an edge portion of the vessel 310 is detected, the first control section 110 performs imaging and illumination control while imaging is performed. In the above description, after the scan in the X direction is ended, the imaging unit 120 is moved in the Y direction by a predetermined amount. Similarly, the imaging unit 120 may be moved in the X direction by a predetermined amount after the scan in the Y direction is ended.

Advantage of Second Embodiment

In this embodiment, even in a part near the edge portion of the vessel for the sample 300, the first control section 110 can acquire an image and measurement data under appropriate illumination control, for example, by selecting an emitting section that emits illumination light from the four illumination optical systems in the vessel edge detection processing. In comparison with the first embodiment, more appropriate illumination control can be executed, since the second embodiment additionally includes illumination control based on detection of a vessel edge portion in the Y direction and a greater number of emitting sections that can be supplementarily used. The technique of this embodiment allows illumination control based on the relative position between the imaging unit 120 and an object to be observed, and appropriately switches the emitting sections that emit illumination light. Therefore, all of the light sources 184 of the imaging unit 120 need not always be used, and the consumption of energy for operating the measurement system 1 can be reduced. Furthermore, since the technique of this embodiment can execute appropriate illumination control based on detection of a vessel edge portion, the scanning method is not specifically limited. For example, as described above, the imaging unit may be moved by a predetermined amount in the Y or X direction after a scan in the X or Y direction is ended. Alternatively, a scan in the X direction and a scan in the Y direction may be alternately performed.

Modification

Figure 14:
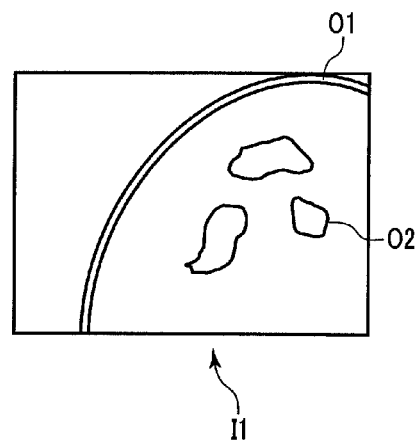
FIG. 14 is a view for explaining a modification of vessel edge detection by image processing.

In the embodiments described above, the first control section 110 detects a vessel edge portion in accordance with a change in brightness value with a change in amount of light acquired by the imaging section 170 based on illumination light emitted from the illumination optical system 182. However, position information of the vessel edge portion may be acquired based on a captured image. FIG. 14 shows a view for explaining a modification of detection of a vessel edge portion by image processing. As shown in FIG. 14, it is assumed that an image I1 acquired by the imaging section 170 includes an object O1 having a regular characteristic, and an object O2 having an irregular characteristic. The characteristic may be an outline or a shape. In this case, the first control section 110 extracts the object having a regular characteristic by analyzing the image, and determines that the object is or may be a vessel edge portion. Image data of various vessels that may be used can be stored in advance as regular characteristics in the first storage section 130 or the second storage section 230. The vessel edge portion may be determined by comparing the captured image data with image data of a vessel read from the first storage section 130 or the second storage section 230.

Depending on an image, the first control section 110 may analyze the image together with an image of an area adjacent to the image, and may comprehensively determine whether or not the object is a vessel edge portion. Depending on a taken image, the first control section 110 may also image an object again after switching illumination by illumination control, and determine whether or not the object is a vessel edge portion based on the newly acquired image. When the first control section 110 cannot determine whether or not the object is a vessel edge portion from results of analyzing the image, imaging may be performed in a plurality of illumination environments by a plurality of illumination controls and the image may be analyzed later together with an image of an area adjacent to the image. Furthermore, the first control section 110 may synthesize images acquired from a wide range while the imaging unit 120 is being moved to show results of observation or measurement. The analysis described above may be performed based on the synthesized image showing the wide range. As described above, the first control section 110 detects the vessel edge portion, and performs illumination control based on a change of an object to be imaged that is included in a newly acquired image or image signal from an object to be imaged that is included in a previously acquired image or image signal; that is, the change may be an appearance of a characteristic in the image indicated by the image signal. At this time, the characteristic is, for example, a regular shape included in the image.

Figure 15:
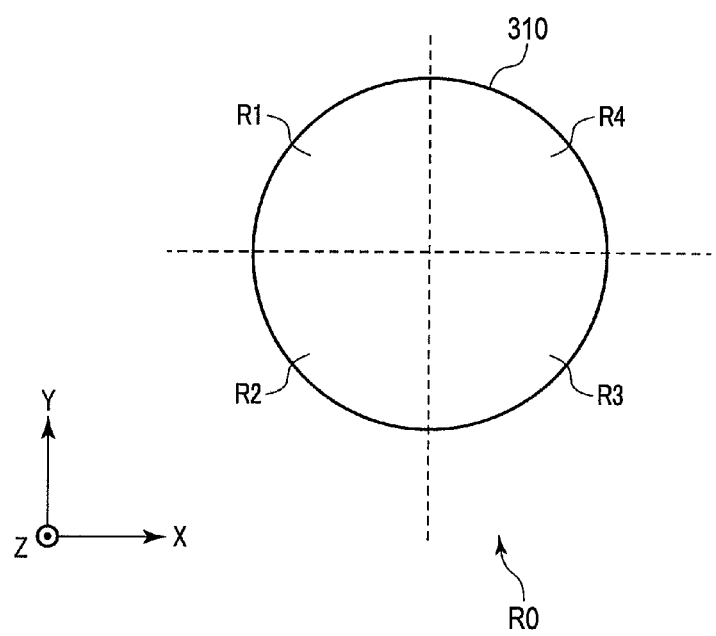
FIG. 15 is a view for explaining a modification of illumination control at a time of image acquisition by an imaging unit.

In the embodiments described above, the first control section 110 performs illumination control based on a change in brightness value. However, after acquiring position information relating to an edge portion of the vessel 310, the first control section 110 may perform illumination control based on position information as described below. FIG. 15 is a view for explaining a modification of illumination control at a time of image acquisition by the imaging unit. It is assumed that the configuration of the imaging unit 120 and the arrangement of the emitting sections are the same as those shown in FIG. 12. For example, as shown in FIG. 15, an observation target range R0 is determined based on position information in the vessel 310. Then, the observation target range R0 is divided into, for example, a first area R1, a second area R2, a third area R3, and a fourth area R4. The first control section 110 acquires a current position of the imaging unit 120, and determines to which area the current imaging range belongs based on the current position and the position information of the vessel 310.

The first control section 110 may perform illumination control based on position information in the following manner. For example, when the imaging unit 120 images a position included in the first area R1, illumination light emitted from the second emitting section 183b or the third emitting section 183c is primary illumination light. Likewise, the first control section 110 uses, for example, the second emitting section 183b or the fourth emitting section 183d in the second area R2, the first emitting section 183a or the fourth emitting section 183d in the third area R3, and the first emitting section 183a or the third emitting section 183c in the fourth area R4. At this time, the first control section 110 may use as supplementary illumination, for example, the first emitting section 183a or the fourth emitting section 183d in the first area R1, the first emitting section 183a or the third emitting section 183c in the second area R2, the second emitting section 183b or the third emitting section 183c in the third area R3, and the second emitting section 183b or the fourth emitting section 183d in the fourth area R4.

When the modification described above is carried out, the fixing frame 410 may be used. A vessel position in accordance with the type of the fixing frame 410 to be used may be stored in advance in, for example, the first storage section 130 or the second storage section 230. The first control section 110 may perform the illumination control described above based on the stored position information of the vessel 310.

Rules of the illumination control are stored in, for example, the first storage section 130 or the second storage section 230. The observation target range R0 is described above as being divided into the four areas to perform illumination control. However, the number of the divided areas is not limited to four. The number of divided areas may be more than one, for example, two or eight. Furthermore, the number of divided areas may be different from the number of illumination optical systems 182 or the number of emitting sections. The number of divided areas may be changed as needed in accordance with the type of a vessel or an observation target. Besides the illumination control based on the divided areas as described above, illumination control may be performed based on coordinates included in the observation target range R0, or coordinates included in the range of movement of the imaging unit 120.

In connection with the above embodiments, reference is made to the case where the observation apparatus 100 processes the images obtained by the imaging section 170 and analyses the measurement results. However, this is not restrictive. The second control section 210 of the controller 200 may perform at least one of these processes if unprocessed data is transferred from the observation apparatus 100 to the controller 200. In other words, an apparatus, as one aspect of the present invention, can be modified in a number of ways. For example, it may be designed to cooperate with a number of apparatuses to attain the above-mentioned functions.

In the above embodiments, reference is made to the case where the transparent plate 102 covers the top of the casing 101 of the observation apparatus 100, and the sample 300 is placed on top of the casing 101. However, this is not restrictive. Depending upon the size of the object to be observed and the shape of the casing, the transparent plate need not be employed. The casing may be just a hollow member. The shape of the observation apparatus 100 may be properly varied in accordance with the shape of the sample 300, the observation direction, or the like.

Furthermore, in the embodiments described above, the vessel 310 of the sample 300 is a transparent vessel including a part that is transparent to illumination light, and an object to be observed is placed in the transparent vessel. However, this is not restrictive. For example, depending on the object to be observed, even if a transparent vessel is not used, the first control section 110 can detect an edge portion of the object to be observed based on scattering of illumination light by the object itself to perform illumination control. The object to be observed is not limited to a cell. For example, the technique of the embodiments can also be applied to inspection of a material surface, if the object to be observed scatters or reflects illumination light.

A change of the order of the processing or the steps in each processing illustrated by the flowcharts is possible. Addition or deletion of a processing or a step is also possible. The processing is executed by the corresponding programs stored in the first storage section 130 or the second storage section 230. Each of the programs may be stored in advance in the measurement system 1 or may be stored in another storage medium. The programs may be stored in various ways in the measurement system 1 or another storage medium; they may be stored before shipment, may be stored in a distributed storage medium, or may be stored through a communication line, such as the Internet.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An observation apparatus comprising:
   an imaging unit comprising:
      an imaging section that includes an image sensor and an imaging optical system, and that images a sample in a vessel to output an image signal; and
      an illumination section that includes a plurality of light sources which are located away from an optical axis of the imaging optical system and configured to emit illumination light toward the sample; and
   a processor that controls operations of the imaging section and the illumination section,
   wherein the plurality of light sources emit the illumination light obliquely upward from below the sample, the illumination light obliquely emitted is reflected obliquely downward by an upper surface of the vessel placed on top of the sample, transmitted through the sample, and enters the imaging section, and
   the processor determines a lighting light source of the plurality of light sources and causes the lighting light source to light based on the image signal.

2. The observation apparatus according to claim 1, wherein the imaging optical system and the plurality of light sources are arranged on a surface of the imaging unit that faces the sample so that the imaging optical system is arranged between the plurality of light sources.

3. The observation apparatus according to claim 1, wherein the plurality of light sources are arranged at symmetrical positions with respect to the image sensor.

4. The observation apparatus according to claim 1, wherein the processor detects a vessel edge portion based on a change of the image signal, and determines the lighting light source of the plurality of light sources so as not to cause the illumination light to be scattered by the vessel edge portion.

5. The observation apparatus according to claim 1, further comprising a driving mechanism that moves the imaging unit, wherein
   the processor controls operations of the driving mechanism, and
   the processor determines the lighting light source of the plurality of light sources based on the image signal, when the imaging unit is moved by the driving mechanism.

6. The observation apparatus according to claim 5, wherein the processor switches the lighting light source when the image signal changes, while a subset of the plurality of light sources which are arranged in a direction of a forward movement side of the imaging unit are lit.

7. The observation apparatus according to claim 5, wherein the control section processor determines the lighting light source based on a change in brightness value included in the image signal in accordance with movement of the imaging unit.

8. The observation apparatus according to claim 7, wherein when the processor detects a decline of the brightness value as the imaging unit moves, the processor switches the lighting light source.

9. The observation apparatus according to claim 5, wherein the processor determines the lighting light source based on a change that is an appearance of a characteristic in the image indicated by the image signal in accordance with movement of the imaging unit.

10. The observation apparatus according to claim 9, wherein when the processor detects a regular shape included in the image while the imaging unit moves, the processor switches the lighting light source.

11. The observation apparatus according to claim 5, wherein the driving mechanism comprises at least one feed screw.

12. A method for controlling an observation apparatus comprising:
   causing an imaging section including an image sensor and an imaging optical system to image a sample in a vessel;
   causing the imaging section to output an image signal acquired by imaging;
   in an illumination section that includes a plurality of light sources located away from an optical axis of the imaging optical system, causing the plurality of light sources to emit illumination light obliquely upward from below the sample, the illumination light obliquely emitted being reflected obliquely downward by an upper surface of the vessel placed on top of the sample, transmitted through the sample, and entering the imaging section, and determining a lighting light source of the plurality of light sources;

causing the lighting light source to light; and wherein the determining is carried out based on the image signal.

13. The method according to claim 12, further comprising:

detecting a vessel edge portion based on a change of the image signal; and determining the lighting light source of the plurality of light sources so as not to cause the illumination light to be scattered by the vessel edge portion.

14. The method according to claim 12, further comprising:

causing the imaging section to move; and determining the lighting light source of the plurality of light sources based on the image signal, when the imaging section is moved.

15. A non-transitory computer-readable medium storing a control program for an observation apparatus to cause a computer to execute:

causing an imaging section including an image sensor and an imaging optical system to image a sample in a vessel;

causing the imaging section to output an image signal acquired by imaging;

in an illumination section that includes a plurality of light sources located away from an optical axis of the imaging optical system, causing the plurality of light sources to emit illumination light obliquely upward from below the sample, the illumination light obliquely emitted being reflected obliquely downward by an upper surface of the vessel placed on top of the sample, transmitted through the sample, and entering the imaging section, and determining a lighting light source of the plurality of light sources;

causing the lighting light source to light; and wherein the determining is carried out based on the image signal.

16. The non-transitory computer-readable medium according to claim 15, further causing the computer to execute:

detecting a vessel edge portion based on a change of the image signal; and determining the lighting light source of the plurality of light sources so as not to cause the illumination light to be scattered by the vessel edge portion.

17. The non-transitory computer-readable medium according to claim 15, further causing the computer to execute:

causing the imaging section to move; and determining the lighting light source of the plurality of light sources based on the image signal, when the imaging section is moved.

* * * * *